US 6,731,384 B2

(12) United States Patent
Ohshima et al.

(10) Patent No.: US 6,731,384 B2
(45) Date of Patent: May 4, 2004

(54) APPARATUS FOR DETECTING FOREIGN PARTICLE AND DEFECT AND THE SAME METHOD

(75) Inventors: Yoshimasa Ohshima, Yokohama (JP); Minori Noguchi, Mitsukaido (JP); Hidetoshi Nishiyama, Fujisawa (JP); Kenji Mitomo, Sakai (JP); Takashi Okawa, Fujioka (JP); Akira Hamamatsu, Yokohama (JP); Shinichi Suzuki, Kodama (JP)

(73) Assignees: Hitachi, Ltd., Tokyo (JP); Hitachi Electronics Engineering Co., Ltd., Tokyo (JP)

( * ) Notice: Subject to any disclaimer, the term of this patent is extended or adjusted under 35 U.S.C. 154(b) by 115 days.

(21) Appl. No.: 09/973,000

(22) Filed: Oct. 10, 2001

(65) Prior Publication Data
US 2002/0041374 A1 Apr. 11, 2002

(30) Foreign Application Priority Data
Oct. 10, 2000 (JP) .......................... 2000-309626
Dec. 21, 2000 (JP) .......................... 2000-388628

(51) Int. Cl.$^7$ .............................................. G01N 21/00
(52) U.S. Cl. ............................... 356/237.2; 356/237.1; 250/559.31
(58) Field of Search .................... 356/237.1–237.6, 356/239.1, 239.3, 239.7, 394; 250/559.29, 559.31

(56) References Cited
U.S. PATENT DOCUMENTS 4,794,264 A * 12/1988 Quackenbos et al. .. 250/559.48
5,410,400 A * 4/1995 Shishido et al. ......... 356/237.4
5,712,701 A * 1/1998 Clementi et al. ........ 356/237.2
5,798,829 A * 8/1998 Vaez-Iravani ............ 356/237.1
6,104,481 A * 8/2000 Sekine et al. ............ 356/237.5
6,118,525 A * 9/2000 Fossey et al. ............ 356/237.2
6,201,601 B1 * 3/2001 Vaez-Iravani et al. ... 356/237.4
6,256,093 B1 * 7/2001 Ravid et al. ............. 356/237.2
6,271,916 B1 * 8/2001 Marxer et al. ........... 356/237.3
6,384,910 B2 * 5/2002 Vaez-Iravani et al. ... 356/237.2
6,411,377 B1 * 6/2002 Noguchi et al. ......... 356/237.4
6,538,730 B2 * 3/2003 Vaez-Iravani et al. ... 356/237.2

FOREIGN PATENT DOCUMENTS

JP          09 210 918      *   8/1997
JP          09 304 289      *  11/1997
JP          2002-162141     *   6/2001

* cited by examiner

Primary Examiner—Frank G. Font
Assistant Examiner—Sang Hoang Nguyen
(74) Attorney, Agent, or Firm—Antonelli, Terry, Stout & Kraus, LLP

(57) ABSTRACT

An apparatus and method for detecting foreign particle and defect on an object in detection by means of a laser beam, in which the laser beams of different wavelengths are irradiated onto the surface of the object in detection from different angles and the state of foreign particle and defect is separately detected according to the output level of the scattered light reflected from that surface. Further, it is arranged such that the scattered light reflected from the object onto which the laser beam is irradiated from the sole source or the plurality of sources is detected in plural directions, which detecting result is compared for the detection of the directivity of said scattered light in reflection.

18 Claims, 17 Drawing Sheets

• CATEGORY A
× CATEGORY B

APPARATUS FOR DETECTING FOREIGN PARTICLE AND DEFECT AND THE SAME METHOD

BACKGROUND OF THE INVENTION

1. Field of the Invention

The present invention relates to a technique for detecting minute foreign particle and defect that might be found on a thin film substrate, a semiconductor substrate or a photomask and so forth.

2. Description of the Prior Art

In the production line of a semiconductor substrate or a film substrate and so on, detection is carried out for foreign particle that is attached on the same substrates so as to monitor the dust contamination in ambient caused by the production apparatus. For instance, it is required to detect such minute foreign particle and defect as is below 0.1 lm in size on the surface of the semiconductor substrate before circuit layout is formed thereon. As one example of the prior art for detecting minute foreign particle and defect on such sample object as the semiconductor substrate, it is disclosed in the specification of the U.S. Pat. No. 5,798,829 that laser beams that are converged within the range from a few lm to several tens of $\mu$m are irradiated against a sample object and scattered light, which is generated from foreign particle when the same matter attaches on the substrate, is detected and the foreign particle and defect on the whole surface of the sample object are detected through the revolution as well as the rectilinear forwarding of the same object.

Further, such concave defects as crystal defect and scratches are found on the surface of the semiconductor substrate. In order to separately detect such concave defects from convex such defect as foreign particle, it is disclosed in Japanese Patent Application Laid-open Nos. 9-304289 and 9-210918 that detection is carried out by changing the irradiation angle of the laser beams or detection angle with regard to a sample object and the detection results are compared so as to classify the defects into some categories.

In accordance with the trend for the high density and large caliber of a semiconductor substrate, a thin film substrate or a photomask and so forth, the means to detect foreign particle and defect on the surface thereof require high sensitivity and high speed for detection. Further, in accordance with the trend for the high density of the semiconductor substrate (semiconductor wafer), the thin film substrate or the photomask and so forth, leveling operation by means of CMP (Chemical Mechanical Polishing) is performed thereon for the purpose of abating the load charged by the depth of focus of an exposure device, in which operation such minute defect as called scratch happens to occur on the surface of the substrate and so forth. The countermeasure taken against the scratch and that against the foreign particle differ, so that it is required to separately detect such scratch from the foreign particle.

The present invention is intended to reduce the number of detection steps so as to perform the detection for a short period of time and to scan a sample object in detection with high speed as well as to accurately grasp the situation of foreign particle and defect with high sensitivity and to separately and precisely detect on such sample object as a semiconductor wafer such defect as scratch from the foreign particle.

SUMMARY OF THE INVENTION

The present invention provides a method for detecting foreign particle and defect and the same apparatus that realize the above purposes.

That is, in this invention, the situation of foreign particle and defect is discerned according to a signal obtained by converting the scattered light of every wavelengths that emits from a sample object into an electric signal upon the irradiation of the plurality of laser beams with different wavelengths with regard to practically the same location of a sample object from different angles. Further, it is arranged such that the laser beams are irradiated onto the sample object from the sole location or several locations and the scattered light emitted from the sample object is detected at several directions, the result of which detection is compared so as to detect the directivity of the scattered light, according to which directivity the foreign particle or defect is separately detected. The above operational steps allow the detection to be carried out with high speed as well as high sensitivity and to separately detect such defect as scratch from foreign particle.

DETAILED DESCRIPTION OF THE INVENTION

Hereinafter, the preferred embodiments of the present invention are described below with reference to the accompanying drawings.

Figure 1:
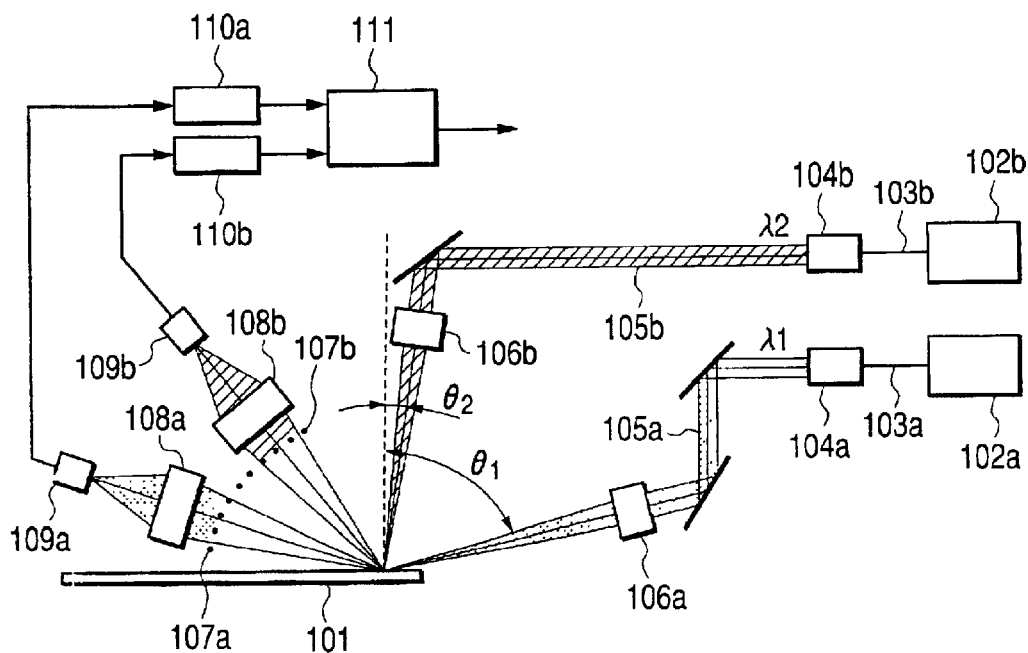
FIG. 1 is a view to show a first embodiment of the present invention.

It is noted that the following embodiments take a semiconductor wafer as an example of an object in detection. FIG. 1 shows the first embodiment of the present invention.

Figure 2:
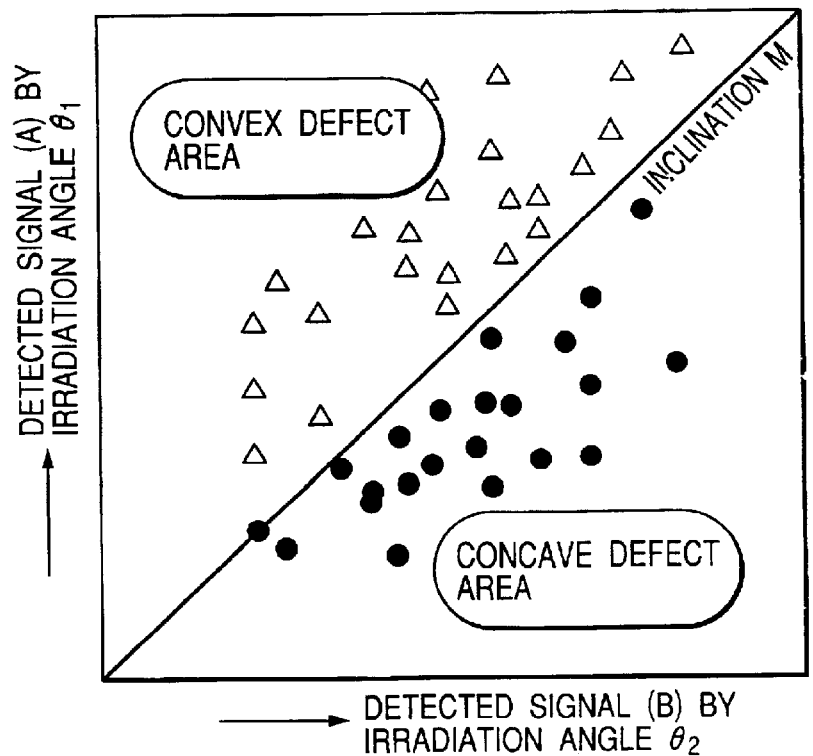
FIG. 2 is a view to show an example to discern concave defect from convex defect according to the present invention.

The arrangement of this embodiment comprises an illumination optical system, a semiconductor wafer for an object in detection, a detection optical system, a photoelectric conversion device, a signal processing circuit and an object in detection scanning means (not shown in the drawings). The above illumination optical system comprises two optical systems with different illumination angle, each of which optical system has a different wavelength. The laser beam 103a with $\ddot{e}_1$ in wavelength that is emitted from a laser luminous source 102a is enlarged in diameter by a beam expander 104a, after which the laser beam as enlarged is converged to a beam diameter in the order of the range from a few ìm to several tens of $\mu$m by a condenser 106a so as to be irradiated onto the surface of the semiconductor wafer 101. Likewise, the laser beam 103b with $\ddot{e}_2$ in wavelength that is emitted from a laser luminous source 102b is enlarged in diameter by a beam expander 104b, after which the laser beam as expanded is converged to a beam diameter in the order of the range from a few ìm to several tens of $\mu$m so as to be irradiated onto practically the same place on the surface of the wafer 101 as in the above laser beam. The respective irradiation angles (incident angle) $\grave{e}_1$ and $\grave{e}_2$ corresponding to the respective laser beams preferably ranges substantially from 60° to 90° and from 0° to 30°, respectively. When there is foreign particle or defect at a location of the wafer surface where the laser beam is irradiated, the scattered light is generated. A part of the scattered light that has a wavelength $\ddot{e}_1$ is abstracted by a wavelength selective filter element 107a, which part is condensed on the light receiving surface of the photoelectric conversion device 109a at the detection optical system 108a so as to perform photoelectric conversion at the same device 109a. Likewise, photoelectric conversion is performed on the other part of the scattered light that has a wavelength $\ddot{e}_2$ at the photoelectric conversion device 109b. Thereby, the scattered light that is generated as a result of the laser beam irradiation with regard to the same foreign particle or defect from different angles is discerned by wavelength for detection. A signal output from the photoelectric conversion devices 109a and 109b respectively is processed by each signal processing circuit 110a and 110b such that the latter recognize the existence of foreign particle or defect where the signal data overpass a threshold limit value while not recognizing the same where the data are within such limit value. Then, at a discriminant circuit 111, distinction analysis is carried out as to whether the same foreign particle or defect is concave or convex in shape and the degree of contamination is serious or not. Again, this discriminant circuit 111, as shown in FIG. 2, discerns whether foreign particle or defect is concave or not according to the largeness of two detection signals A and B, in which A is a signal detected by the irradiation angle $\grave{e}_1$ while B is a signal detected by the irradiation angle $\grave{e}_2$ and analyzes whether the degree of contamination owing to the foreign particle or defect is serious or not on the basis of the level of the respective detection signals A and B. The boundary (a line with the inclination M (=A/B) as shown in FIG. 2) to discern whether the foreign particle or defect is concave or convex in view of the largeness of the respective detection signals A and B is decided by such parameters of the illumination optical system as the irradiation angles $\grave{e}_1$ and $\grave{e}_2$ and the quantity of light of the respective laser beams, for examples. Provided that the detection signal A is larger than the signal B so that the former covers an area beyond the inclination M of the boundary, the foreign particle or defect is discerned convex in shape while providing that the signal B is larger than the signal A so that the former covers an area below the inclination M thereof, the foreign particle or defect is discerned concave. When the level of the detection signal A is high, the degree of contamination owing to the convex foreign particle or defect is discerned serious while the same degree is discerned minor when it is low. On the other hand, when the level of the detection signal B is high, the degree of contamination owing to the concave foreign particle or defect is discerned serious, in which concave defect is more frequent, while the same degree is discerned minor when it is low.

The above operations are performed along with the operation where the irradiation location of the laser beam with regard to the wafer 101 relatively moves over a certain detection area of the same wafer, which allows foreign particle or defect to be detected and categorized. The relative movement of the irradiation location with regard to the wafer is provided by the combination between the rotational movement of the wafer 101 by means of an object in detection scanning means (not shown in the drawings) and the transferring movement where the rotation axis position of the same wafer gradually approaches the irradiation point of the laser beam, which causes the irradiation location of the laser beam to relatively move with regard to the wafer in a spiral manner.

For the laser luminous sources 102a and 102b as shown in FIG. 1, an Ar laser, a semiconductor laser or a YAS-SHG laser are put to use, for examples. In the detection optical systems 108a and 108b, an optical lens is arranged such that it condenses the scattered light emitted from the wafer 101 into the light receiving surface of the photoelectric conversion devices 109a and 109b, which lens also performs optical processing for the scattered light such as the change and adjustment of optical property by means of a polarized plate and a space filter. The same photoelectric conversion devices 109a and 109b are intended for receiving the scattered light that is condensed by the above optical systems 108a and 108b and for performing the photoelectric conversion of the same light, which include a TV camera, a CCD linear sensor, a TDI (Time Delay Integration), an anti-blooming TDI sensor and a photomultiplier, for instances.

Figure 3:
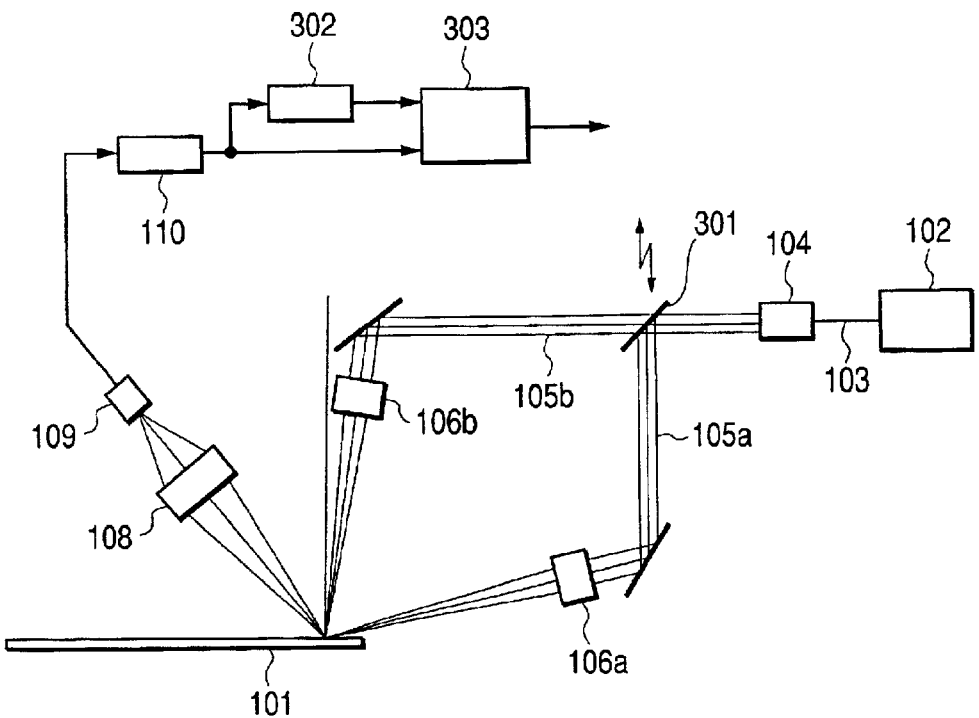
FIG. 3 is a view to show a second embodiment of the present invention.

FIG. 3 shows the second embodiment of the present invention.

In the arrangement as shown in FIG. 3, a laser beam 103 emitted from a laser luminous source 102 turns to become expanded beams 105a and 105b, which beams are irradiated onto the surface of a wafer 101 at condensers 106a and 106b. The illumination angle varies by intervening a mirror 301 in the light path. At the first detection, the whole surface of the wafer 110 is detected by one of the illumination angles and whether there is foreign particle or defect on the surface in comparison with the threshold limit value is discerned at the signal processing circuit 110 wherein provided that the signal data overpass the same value, the circuit 110 recognizes such foreign particle or defect thereon while providing that the data are within the threshold limit value, the circuit disregards such data, and the detection result including coordinates is memorized at a memory circuit 302. At the second detection, the whole surface of the wafer 101 is detected by the other illumination angle and whether there is foreign particle or defect on the surface is discerned in comparison with the threshold limit value at the signal processing circuit 110 in the same way as the first detection, and the detect result as well as the memorized contents in the memory circuit 302 are compared at the discriminant circuit 303 so as to separately detect foreign particle from defect.

Figure 4:
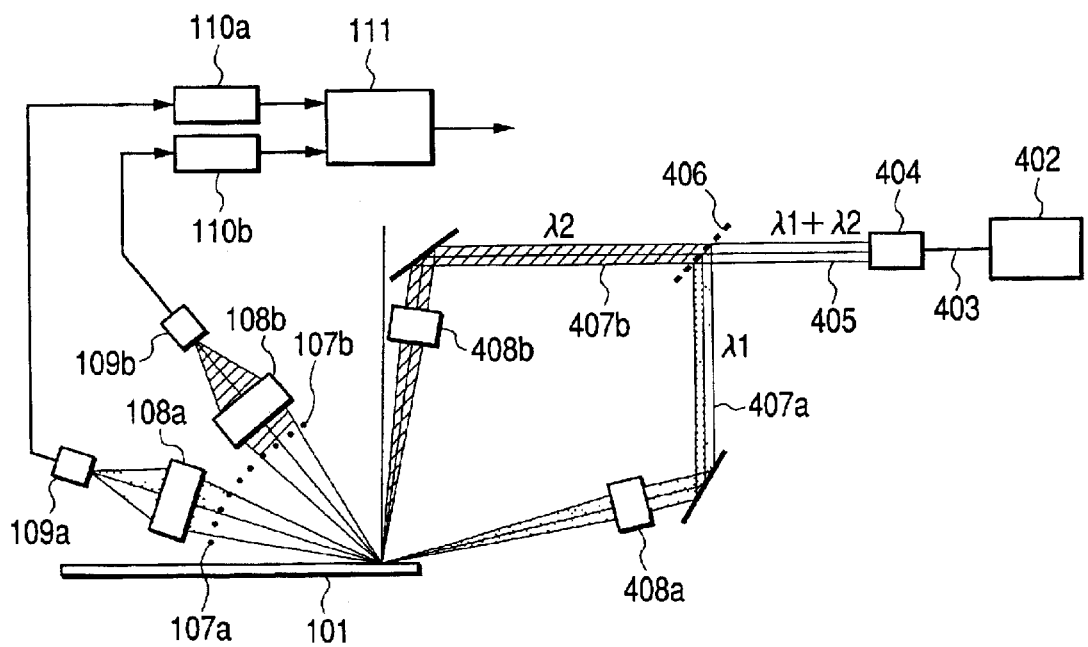
FIG. 4 is a view to show a third embodiment of the present invention.

FIG. 4 shows the third embodiment of the present invention. Such processing steps as irradiating two laser beams with different wavelengths and by different angles onto the surface of the semiconductor surface and detecting the scattered light of each wavelength emitted from the wafer is the same as the first embodiment of the present invention, which is shown in FIG. 1. In the arrangement as shown in FIG. 4, a multi-oscillation laser is adopted for a laser luminous source 402, the wavelengths of which laser beam comprise $\ddot{e}_1$ and $\ddot{e}_2$. The laser beam emitted from the source 402 turns to become a beam 405 that is expanded in diameter at a beam expander 404, which beam 405 is separated into a laser beam path 407a with the wavelength of $\ddot{e}_1$ and a laser beam path 407b with the wavelength of $\ddot{e}_2$ at a wavelength separation mirror 406. Then, those beams are condensed at condensers 408a and 408b so as to irradiate onto the surface of the wafer 101. Thereby, the same effect as the first embodiment is obtained here too.

Figure 5:
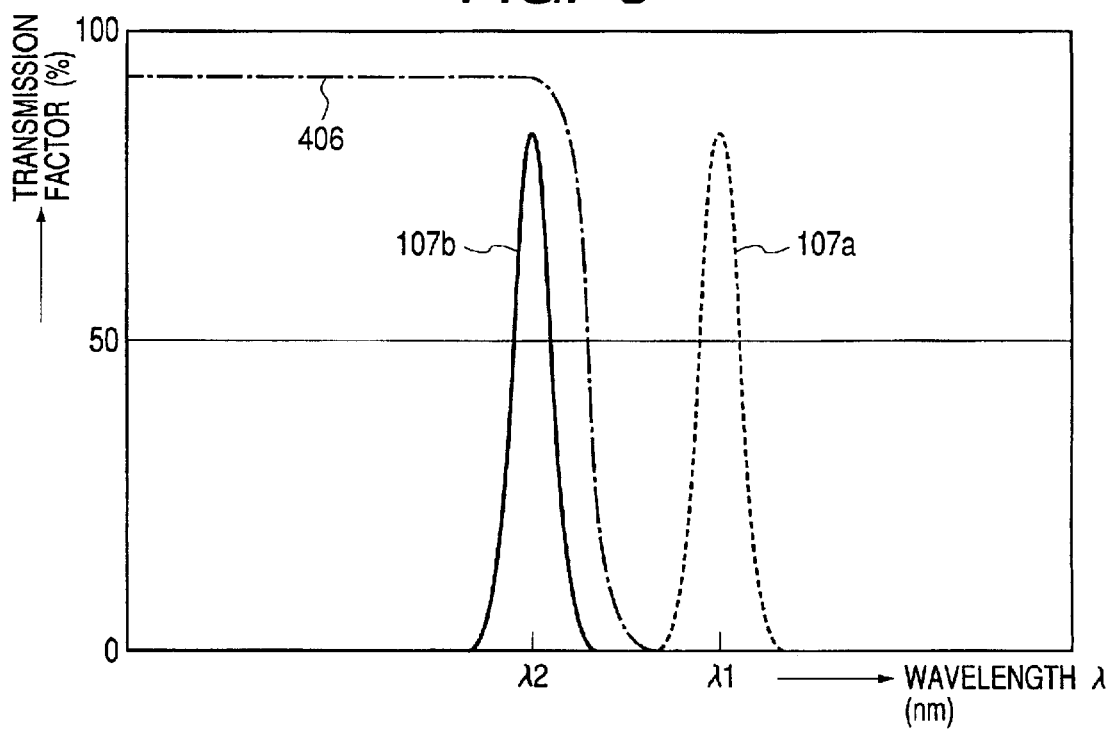
FIG. 5 is a view to explain wavelengths separation means for illumination light in use for the present invention.

FIG. 5 is a view to explain the state where the laser beams are separated into each wavelength at the wavelength separation mirror 406. The separation mirror 406 reflects the laser beam with the wavelength of $\ddot{e}_1$ while transmitting the same with that of $\ddot{e}_2$. A wavelength selective filter 107a transmits the laser beam with the wavelength of $\ddot{e}_1$ while a wavelength selective filter 107b transmits the same with that of $\ddot{e}_2$, which optical characteristics allow foreign particle or defect to be separately detected. In the above third embodiment, it is shown that the multi-oscillation laser comprising two wavelengths is adopted, but there is no difference in effect where a multi-oscillation laser comprising three or more wavelengths is adopted instead, provided that the optical characteristics of the separation mirror and the selective filter shall be modified.

Figure 6:
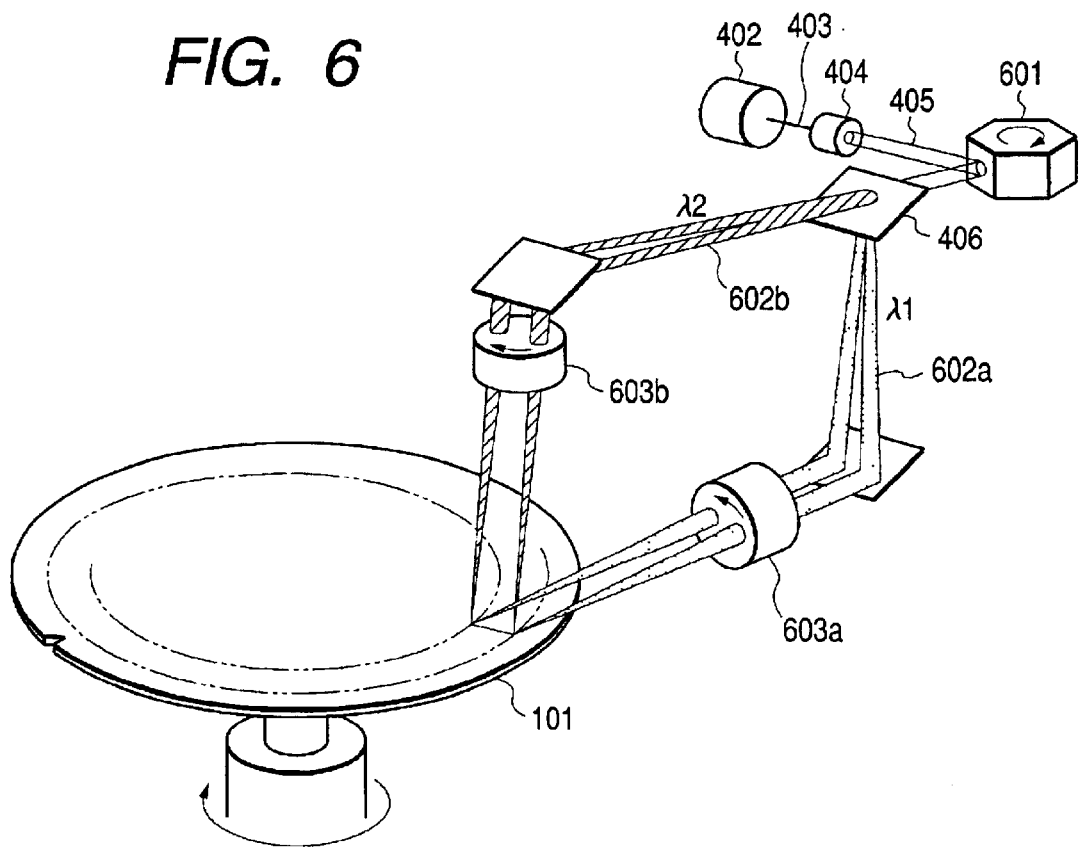
FIG. 6 is a view to show a fourth embodiment of the present invention.

FIG. 6 shows the fourth embodiment of the present invention.

Figure 7:
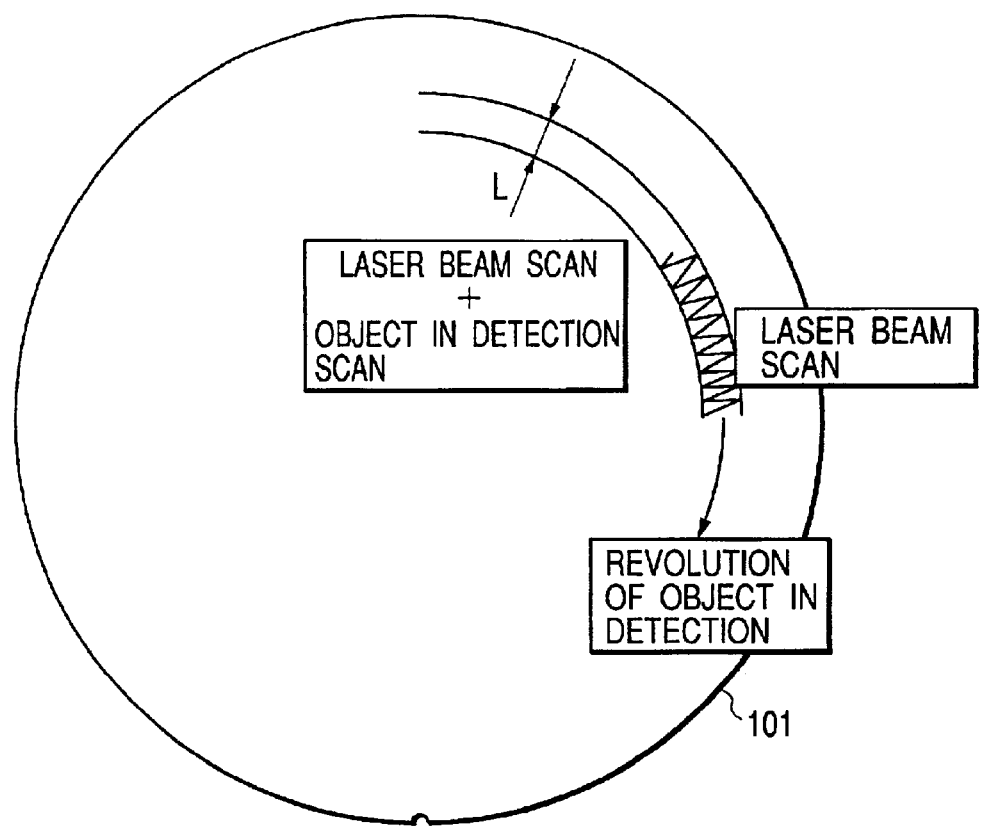
FIG. 7 is a view to explain complex scanning between laser beam scan and object in detection scan according to the present invention.

This embodiment further accelerates the detection speed compared with that of the third embodiment. Such arrangement as separating the laser beam emitted from the multi-oscillation laser 402 into respective laser beams of different wavelength and irradiating those beams onto the surface of the wafer 101 by different angle is the same as the third embodiment, which is shown in FIG. 4. The difference between the third embodiment and this one lies in that the laser beams of two different wavelengths to be irradiated onto the wafer 101 are synchronously scanned. That is, a polygon mirror 601 is arranged in the path of the expanded beam 405 so as to scan the laser beams 602a and 602b, which beams in conversion scan the surface of the wafer 101 through scan lenses 603a and 603b. The relation between the laser beam scanning and the scanning on the surface of the wafer 101 in this embodiment is shown in FIG. 7. This embodiment adopts the complex scanning between the spiral scan on the surface of the wafer 101 and the laser beam scanning over the width L. The rectilinear forwarding of the wafer per one revolution upon the spiral scanning thereof is less than the spot diameter of the laser spot that is irradiated onto the wafer 101, provided that the laser beam is immobilized where the same does not perform the scanning operation while providing that the beam performs the same operation, the rectilinear forwarding of the wafer is equivalent to the scanning width (L) of the laser beam. In this embodiment, the scanning speed of the laser beam is faster than the rotational speed of the wafer 101. Thus, it allows the detecting time for the targeted area of the wafer that is an object in detection to be shortened.

Figure 8:
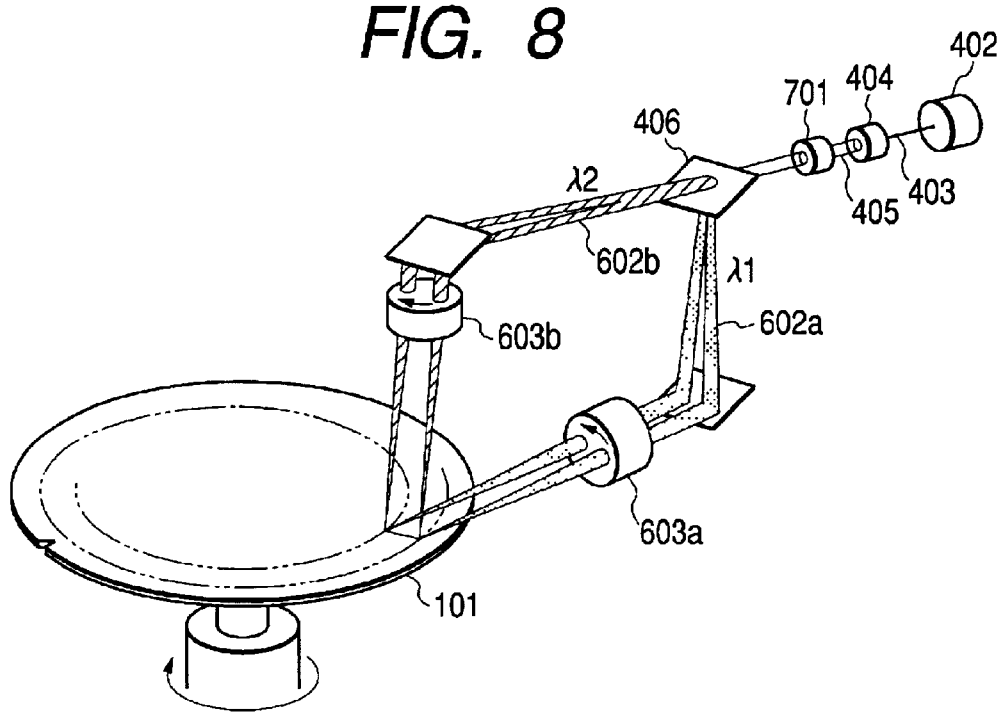
FIG. 8 is a view to show a fifth embodiment of the present invention.

FIG. 8 shows the fifth embodiment of the present invention.

This embodiment is characterized in that the laser beam scanning is carried out by an AOD (Acoustic Optical Deflector) 701. The other arrangement is substantially the same as the fourth embodiment. This embodiment, in the same way as the fourth embodiment, allows the detecting time as mentioned above to be shortened.

Figure 9:
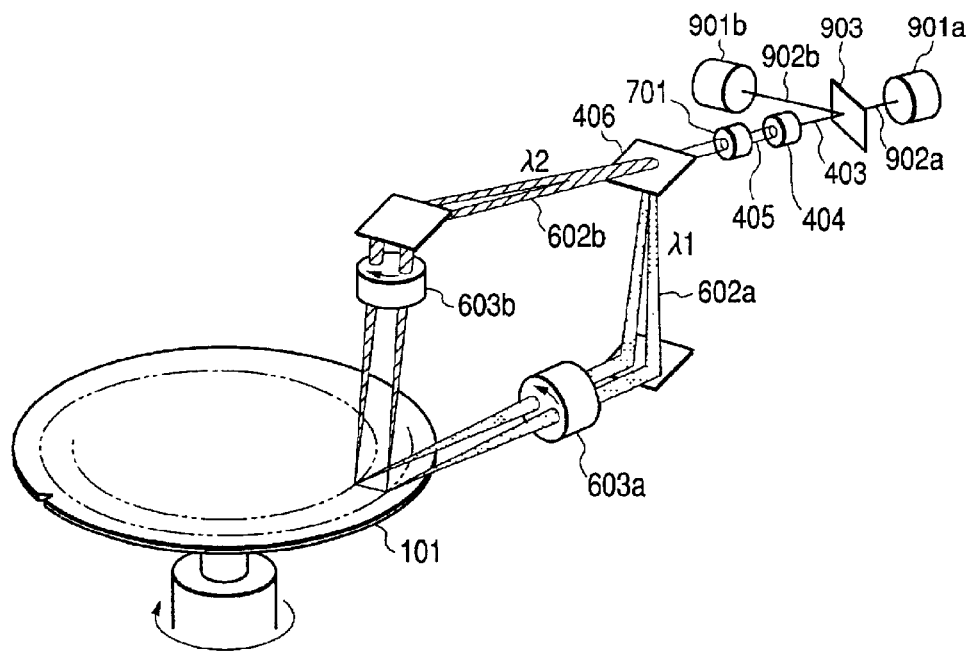
FIG. 9 is a view to show a sixth embodiment of the present invention.

FIG. 9 shows the sixth embodiment of the present invention, which embodiment in the same way as the fifth one is arranged such that the laser beam scanning is carried out by an acoustic optical deflector (AOD) 701, but which is different in that it adopts two single wavelength laser luminous sources (901a and 901b) with different wavelength, the laser beams 902a and 902b emitted from which sources turn to become a single laser beam 904 at a half mirror 903. Instead of this half mirror 903, there is no matter whether a half prism or a wavelength separation mirror is put to use. Also, in case where a linear deflection laser is replaced with the single wavelength laser, provided that the deflecting direction of the laser beams 902a and 902b respectively emitted from the deflection laser are intercrossed with each other, a deflecting plate or a modified prism is adopted.

Figure 10:
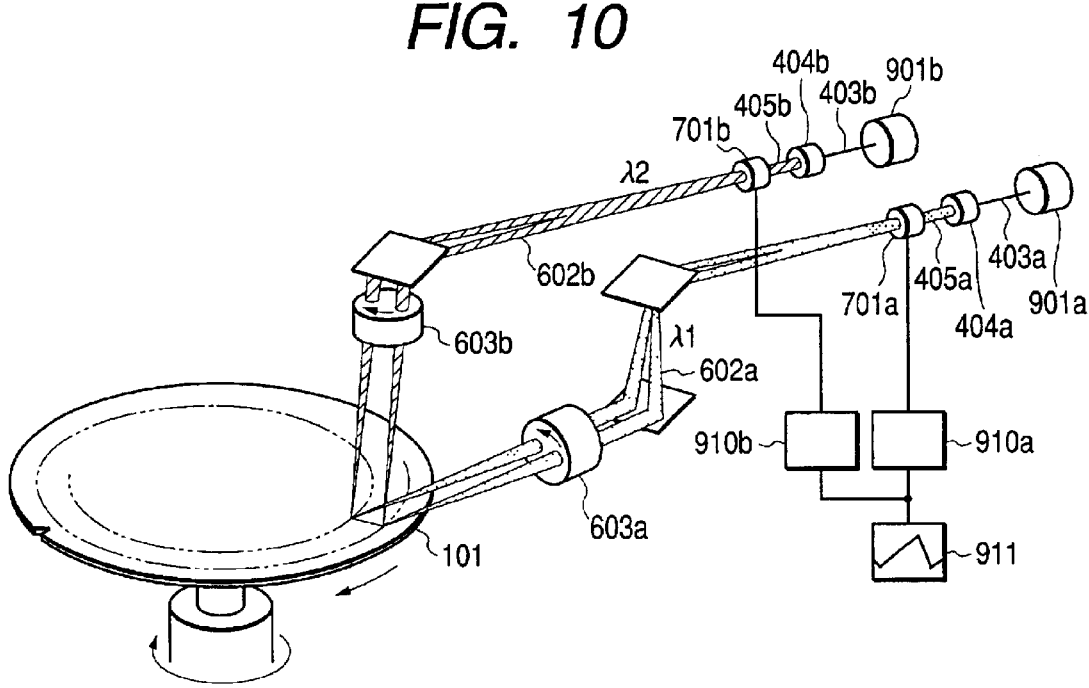
FIG. 10 is a view to show a seventh embodiment of the present invention.

FIG. 10 shows the seventh embodiment of the present invention, which embodiment in the same way as the sixth embodiment is arranged such that the laser beam scanning is performed by the acoustic optical deflector (AOD) 701, but which is different from the sixth embodiment wherein the laser beams scanning of two wavelength are carried out by the sole acoustic optical deflector (AOD) 701 in that the respective acoustic optical deflectors 701a and 701b are provided with the respective single wavelength laser luminous source 901a and 901b so as to scan the respective laser beams 405a and 405b, which deflectors are driven by the respective circuits 910a and 910b on the basis of a signal output from a signal generating circuit 911. Accordingly, when a signal of the same waveform and timing is input to the respective circuits 910a and 910b, the synchronous laser beams scanning operation is performed on the surface of the wafer 101, which allows the detecting time for foreign particle or defect to be shortened.

Figure 11:
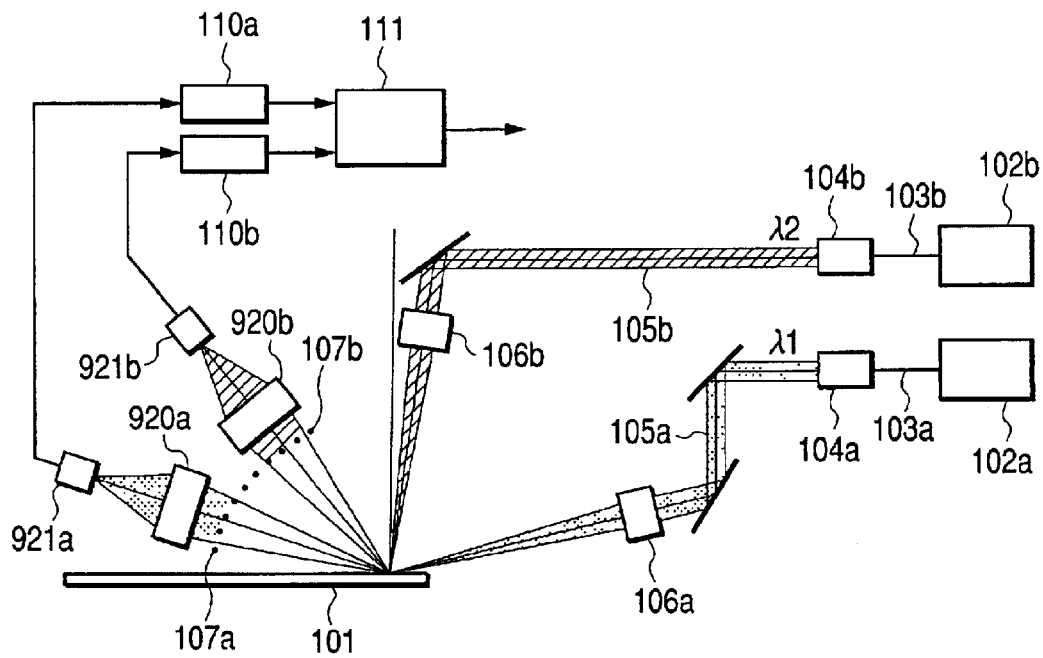
FIG. 11 is a view to show an eighth embodiment of the present invention.

FIG. 11 is a view to show the eighth embodiment of the present invention.

The first to the third embodiments as shown in FIGS. 1, 3 and 4 adopt a condenser for the detection optical system, and the scattered light as generated on the surface of the wafer 101 is condensed on the light receiving surface of the photoelectric conversion device while this embodiment adopts image formation lenses 920a and 920b for the detection optical system as well as a CCD linear sensor or TDI sensor for the photoelectric conversion devices 921a and 921b, which allows the scattered light as generated on the surface of the wafer 101 to be processed as images. Providing that the picture element of the respective photoelectric conversion devices 921a and 921b is rendered small in size, it allows the images to be processed in high resolution, which permits minute foreign particle or defect to be detected. In this case, it is required that the spot size of the irradiated laser beam should correspond to the field of vision of the respective photoelectric conversion devices 921a and 921b.

The respective embodiments as shown in FIG. 1 and FIGS. 4 to 11 are arranged such that a detection optical system and a photoelectric conversion device are separately adopted for the respective irradiation angles of the laser beam. The present invention is not limited to those embodiments, but can be arranged such that the detection optical system and the photoelectric conversion device are consolidated into one group as shown in the second embodiment, which is shown in FIG. 3. In this case, a given detecting result is obtained by performing detection twice.

Figure 12:
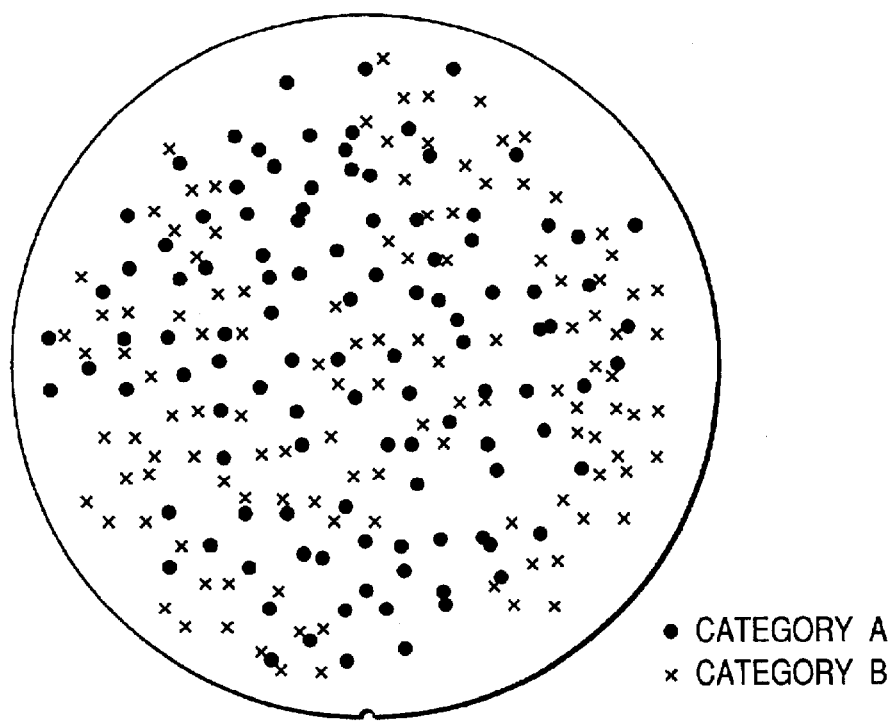
FIG. 12 is an example to indicate the detection result obtained according to the present invention.

FIG. 12 shows an example of the detecting result obtained by the present invention. As described above, the foreign particle or defect is classified into categories for detection according to the present invention, so that the mapping display of the foreign particle and defect with different markings every categories as shown in the example permits us to see the contents and position of the foreign particle or defect at a glance and to grasp the condition of the foreign particle or defect more accurately. The position of the foreign particle or defect is recognized by a position (r) with regard to the radius direction on the plane surface of the wafer and a position (è) with regard to the irradiation angle thereon upon the detection of the foreign particle or defect. The displaying of the detected number of the foreign particle or defects for every category allows us to grasp the situation of foreign particle attachment and occurrence of defect more accurately. Further, the indication of such information as the seriousness of the foreign particle or defect in the above mapping display by the change of the markings in size or in color permits us to grasp more detailed information on such foreign particles and defects, which facilitates the countermeasure against the foreign particle or defect on the wafer, which is an object in detection, to be taken.

Figure 13:
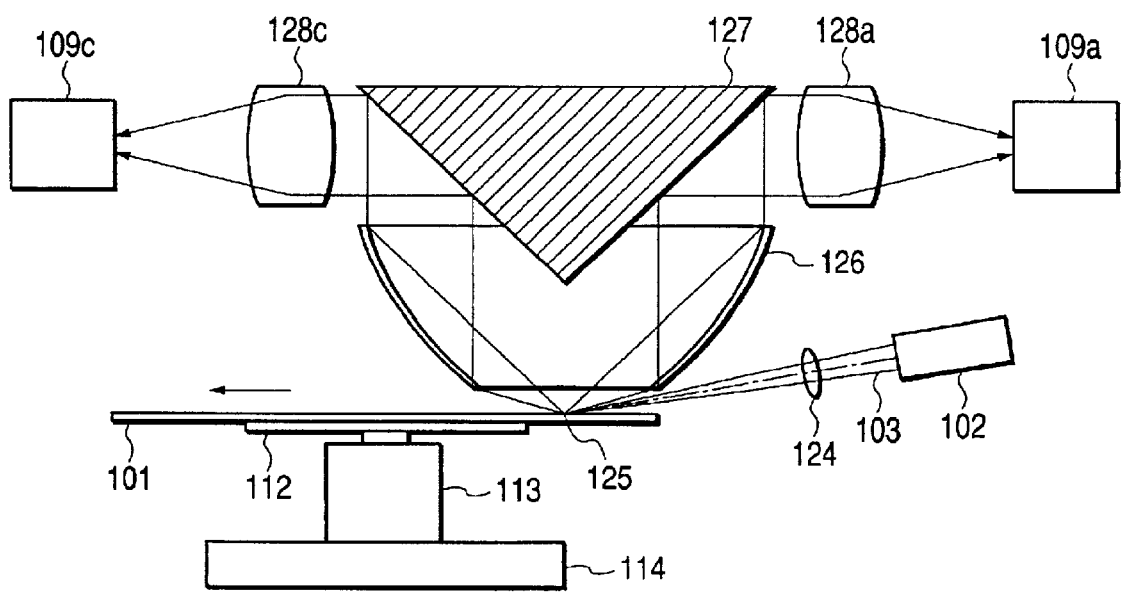
FIG. 13 is a view to show the ninth embodiment of the present invention.
Figure 14:
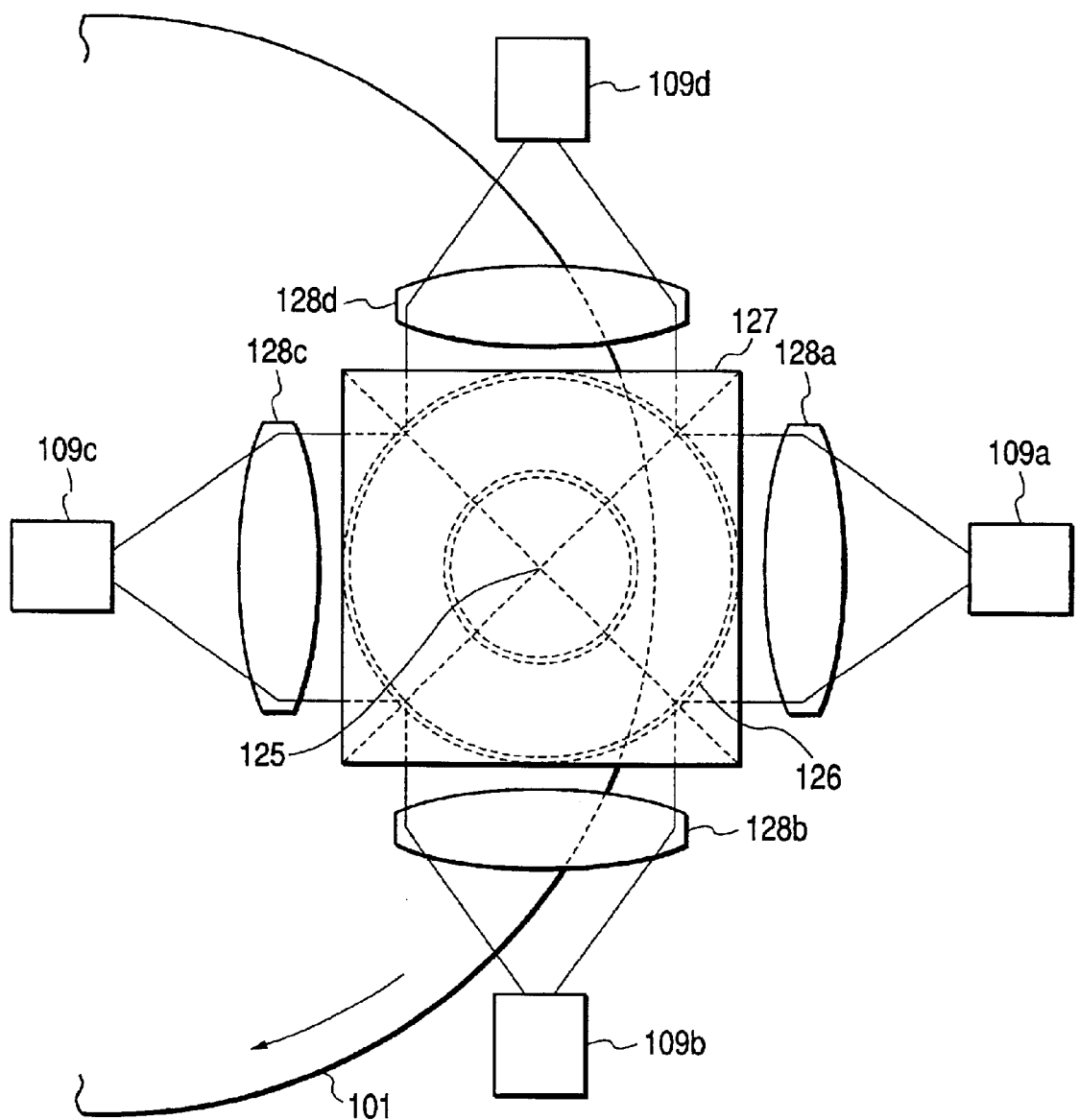
FIG. 14 is a plan view of a ninth embodiment.

FIGS. 13 and 14 show the ninth embodiment of the present invention, which show an apparatus for separately detecting such defect as scratch from foreign particle on the wafer, which is an object in detection. FIG. 13 is a side view thereof while FIG. 14 is a plan view thereof.

This embodiment comprises an illumination optical system, a detection optical system that is one part of detection means to detect scratch and defect and object in detection scanning means. The illumination optical system is provided with a laser luminous source 102 and a condenser 124. The detection optical system is provided with a curved mirror 126, a pyramidal mirror 127, the plurality of or four condensers 128a to 128d and the plurality of or four pieces of photoelectric conversion devices 109a to 109d. The object in detection scanning means is provided with a chuck 112 to hold the wafer 101, a revolution means to rotate the wafer and a rectilinear forwarding means 114 to move rectilinearly the wafer 101 with regard to the radius direction thereof. In the above arrangement, the laser beam at the illumination optical system is irradiated onto a certain position 125 of the wafer surface, the scattered light emitted from which wafer 101 is condensed at the condensers 128a to 128d of the detection optical system. Then, the scattered light as condensed is converted into electrical signals at the respective photoelectric conversion devices 109a to 109d. The respective signals as converted are processed at a signal processing circuit so as to be output as signals corresponding to the directivity of the scattered light. The signals as output are input to a displaying section, where the detecting result of foreign particle or scratch (defect) is separately displayed. Thereby, the detection and distinction or the classification of foreign particle or scratch (defect) to be found on the semiconductor wafer 101 is carried out. To note, upon the above operational steps, the wafer 101 is subjected to the rotational scanning operation and the rectilinear movement in horizontal direction at the object in detection scanning means. Thereby, the surface of the wafer 101 is spirally scanned, in the whole given area of which surface the detection and distinction or the classification of such defect as scratch or foreign particle is carried out. In this embodiment, the curved mirror of the whole surround type effectively condenses the scattered light, so that it enhances the detection sensitivity and precision, which allows us to detect minute scratch or foreign particle on the surface. The illumination optical system is arranged such that the laser beam 103 emitted from such laser luminous source 102 as an Ar laser or a semiconductor laser is irradiated slantingly with regard to the wafer 101, which is called hereinafter slanting illumination, in the sate where the beam is condensed within the range of several tens of $\mu$m by the condenser 124, so that it is adjusted that the beam is irradiated at the focal point of the detection optical system. The laser beam irradiation angle of the slanting illumination is preferred to have the angle of elevation within the range from 0° to 15°. Now, the detection optical system is provided with a curved mirror 126, a pyramidal mirror 127 and condensers 128a to 128d so that the scattered light from the wafer 101 is condensed at the positions of the photoelectric conversion devices 128a to 128d, in which system such optical processing for the scattered light as the change or adjustment of optical property by means of a polarizing plate or a space filter. For the photoelectric conversion devices 109a to 109d, a TV camera, a CCD linear sensor, a TDI (Time Delay Integration) sensor, an anti-blooming TDI sensor or a photomultiplier are adoptable, for instances. In this embodiment, a target position 125 on the surface of the wafer is adjusted such that it corresponds to the focal point of the curved mirror 126. Thus, a part of the scattered light that is generated at the focal point to be incident to the curved mirror 126 reflects vertically upwards with regard to the plane surface of the wafer, which part is further separated into four directions at the pyramidal mirror 127 and which is condensed on the light receiving surface of the respective photoelectric conversion devices 109a to 109d at the respective condensers 128a to 128d so as to be converted into electrical signals.

Figure 15:
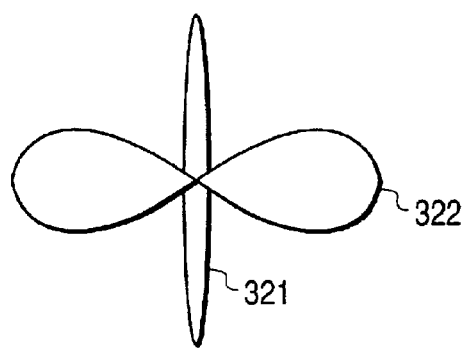
FIG. 15 is a view to explain the directivity of the scattered light.

FIG. 15 is an exemplary view to show the directivity of the scattered light that is generated by a defect, when the laser beam is irradiated onto such defect on the wafer.

The scattered light 322 that is generated at a scratch 321 with directivity longitudinally and at both sides of the scratch distributes in intensity. The distribution form of the directivity differs according to the shape and size of the scratch. On the other hand, the scattered light emitted from a foreign particle with the size of 0.1 ìm or less has no directivity and omnidirectionally distributes in intensity. Accordingly, the detection of the existence and degree (distribution form and so forth) of the directivity of the scattered light allows us to distinguish defect such as scratch from foreign particle and to know the size thereof and so on.

Figure 16:
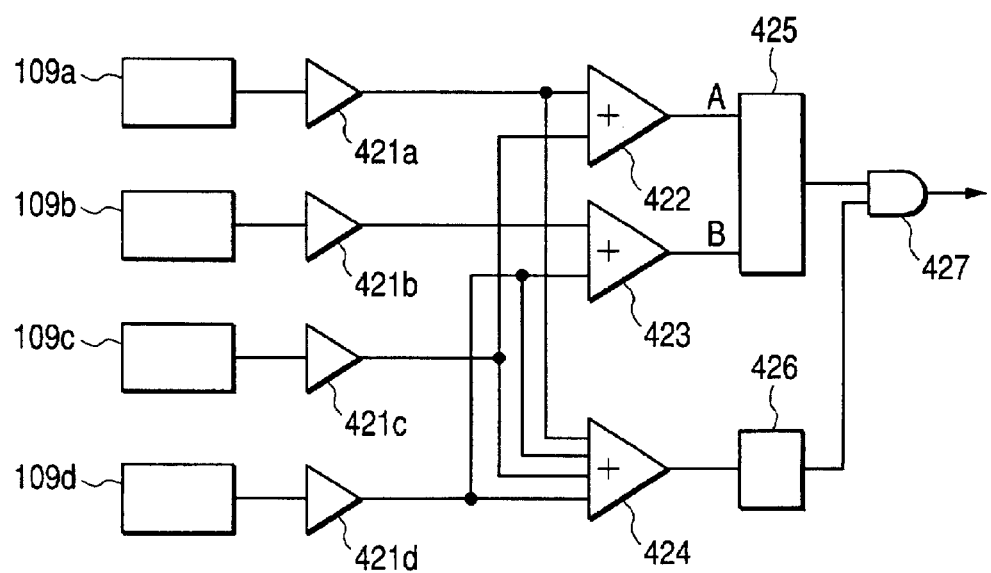
FIG. 16 is a view to show a signal processing circuit of the ninth embodiment.

FIG. 16 shows an example of a signal processing circuit to detect the directivity of the scattered light in reflection.

In FIG. 16, analog processing circuits 421a to 421d amplify an output from the respective photoelectrical conversion devices 109a to 109d and perform the noise processing operation and so forth. The output values of the respective analog processing circuits 421a to 421d are summed up at summing circuits 422 and 423, which is compared at a comparison circuit 425. When the relation between the output A of the summing circuit 422 and that B of the summing circuit 423 is defined as |A−B|>k, the scattered light in reflection has directivity, so that the source to generate the scattered light is found to be defect such as scratch. In the present circuit arrangement, in order to avoid the mistake of the detecting result owing to noise, it is arranged such that after the output of the respective analog processing circuits 421a to 421d is summed up at a summing circuit 424, the summing result is input to a comparison circuit 426, and when the result is more than a give value, it is found to be foreign particle or defect such as scratch. It is arranged such that the output of the comparison circuit 426 and that of the above comparison circuit 425 are input to an AND gate 427, and the latter output is controlled by the former output.

The ninth embodiment of the present invention permits us to detect defect such as scratch and foreign particle on the wafer in an accurate and fast manner with the exclusion of the affect of noise. Further, the arrangement of the reflection optical system by means of the curved mirror of the whole surround type maximizes the usage of the scattered light in reflection so as to enhance the detection sensitivity, with the result that even a defect or foreign particle of minute size is separately detected.

Figure 17:
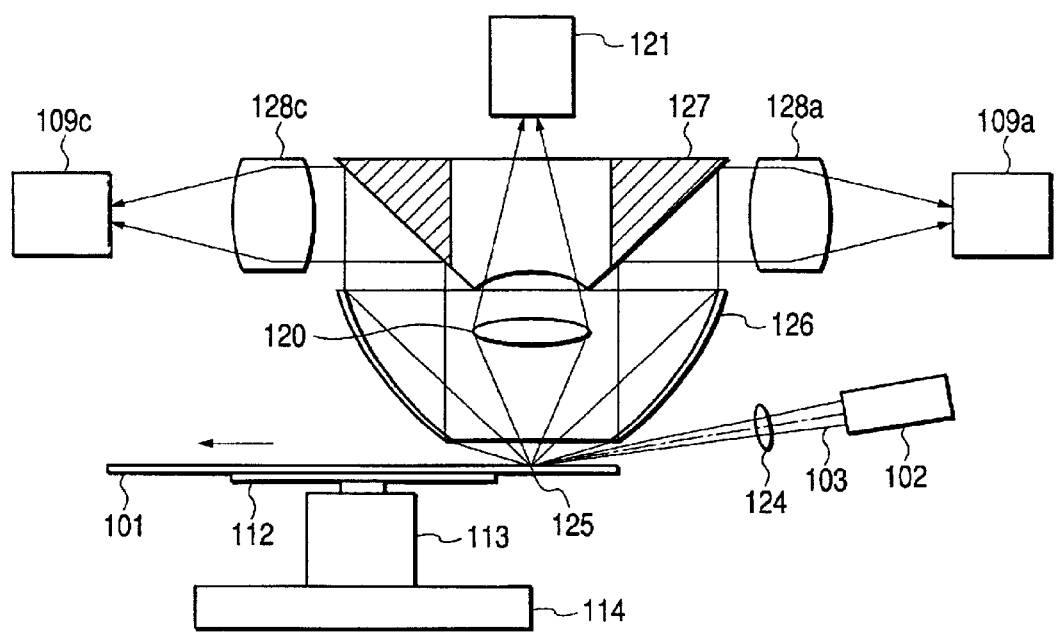
FIG. 17 is a view to show a tenth embodiment of the present invention.
Figure 18:
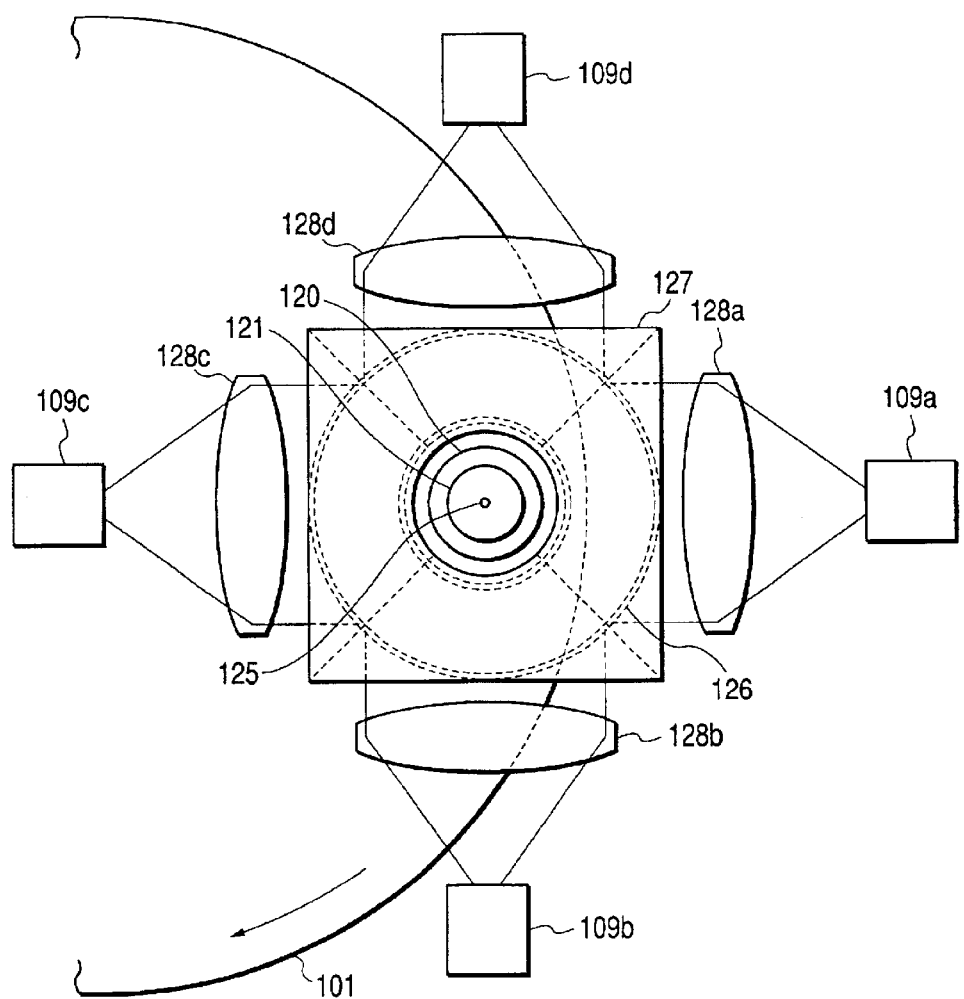
FIG. 18 is a plan view of the tenth embodiment of the present invention.
Figure 19:
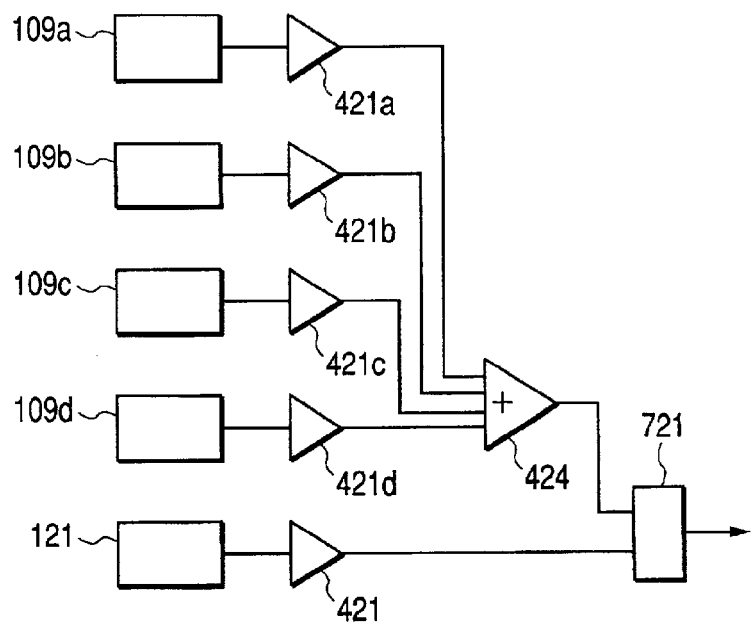
FIG. 19 is a view to show a signal processing circuit of the tenth embodiment.

FIGS. 17, 18 and 19 show the tenth embodiment of the present invention, among which FIGS. 17 and 18 show the side view and the plan view thereof while FIG. 19 shows an example of a signal processing circuit arrangement.

This embodiment is characterized in that the directivity of the scattered light to be reflected in the substantially vertical direction with regard to the plane surface of the wafer 101 and that of the scattered light to be reflected around the circumference of the wafer and be incident to the curved mirror 126 are detected, on the basis of which the detection of scratch or foreign particle is carried out. In FIGS. 17 and 18, the scattered light to be reflected in the substantially vertical direction with regard to the plane surface of the wafer 101 is condensed at a condenser 120 and is incident to a photoelectric conversion device 121 through a central hole of a pyramidal mirror 127 so as to be converted into an electrical signal. The arrangement and the operation of the curved mirror 126, the pyramidal mirror 127, the condensers 128a to 128d and the photoelectric conversion devices 109a to 109d are the same as those of the above ninth embodiment. The processing of the output signal from the respective photoelectric conversion devices is carried out at a signal processing circuit as shown in FIG. 19. In FIG. 19, amplification and noise processing operation and so forth are carried out for the output from the respective photoelectric conversion devices 109a to 109d at the respective analog processing circuits 421a to 421d, and the output of the respective analog processing circuits 421a to 421d is summed up at the summing circuit 424. Amplification and noise processing operation and so forth are carried out for the output from a photoelectric conversion device 121 at an analog processing circuit 421. The output from the analog processing circuit 411 and that of the summing circuit 424 are compared at a comparison circuit 721. The operation result is output to the displaying section, in which section whether the source to generate the scattered light is defect such as scratch or foreign particle is separately displayed.

This embodiment also utilizes the scattered light to be reflected in the substantially vertical direction with regard to the plane surface of the wafer 101 for detection purposes so as to detect a scratch or foreign particle with high sensitivity. The provision of an aperture arranged in the central portion of the pyramidal mirror 127 lightens the same mirror itself. The other operations and effect are the same as those of the above ninth embodiment.

Figure 20:
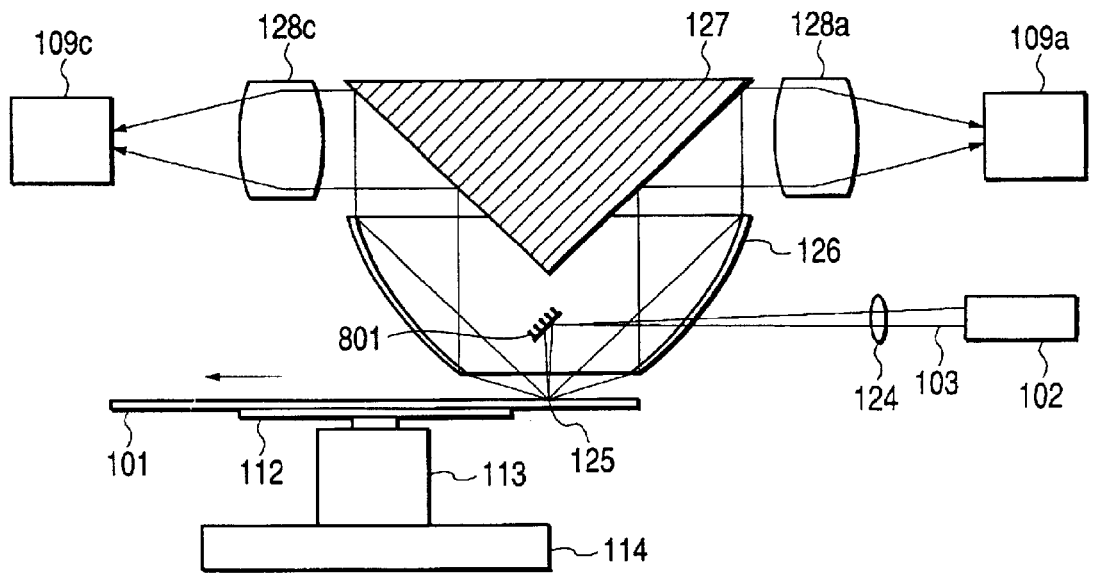
FIG. 20 is a view to show an eleventh embodiment of the present invention.

FIG. 20 shows the eleventh embodiment of the present invention.

This embodiment is characterized in that the laser beam is incident with regard to the plane surface of the wafer 101 from the substantially vertical upper direction, which beam is introduced substantially in parallel with regard to the plane surface of the wafer through the aperture provided on the side surface of the curved mirror 126. Thereafter, the beam is reflected in the substantially vertical direction with regard to the wafer at a mirror 801. The processing method of the scattered light reflected from the wafer 101 is the same as that of the above ninth embodiment including the signal processing as well as the displaying of the processing result.

According to this embodiment, the laser beam is irradiated from the substantially vertical upper direction with regard to the plane surface of the wafer 101, which allows the whole surface of such defect as concave scratch to be subjected to the laser beam. Thus, it facilitates the detection of such defect as above. The other operations and effects are the same as those of the above ninth embodiment.

Figure 21:
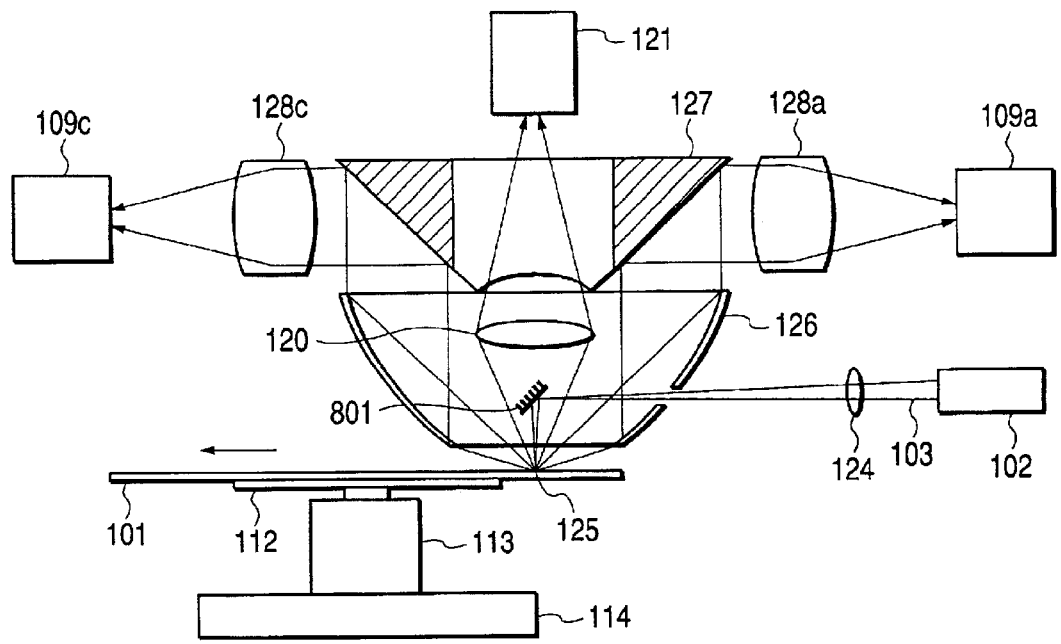
FIG. 21 is a view to show a twelfth embodiment of the present invention.

FIG. 21 shows the twelfth embodiment of the present invention, which embodiment is arranged such that the laser beam is irradiated from the substantially vertical upper direction with regard to the plane surface of the wafer 101 in the same way as the above eleventh embodiment, and the directivity of the scattered light in reflection is detected and displayed for the detection of defect such as scratch or foreign particle in the same way as the tenth embodiment thereof.

This embodiment especially facilitates the detection of defect such as concave scratch in the same way as the eleventh embodiment while in the same way as the tenth embodiment allowing such scratch or foreign particle to be detected with high sensitivity and the pyramidal mirror 127 to be rendered light in weight. The other operations and effects are the same as those of the above ninth embodiment.

Figure 22:
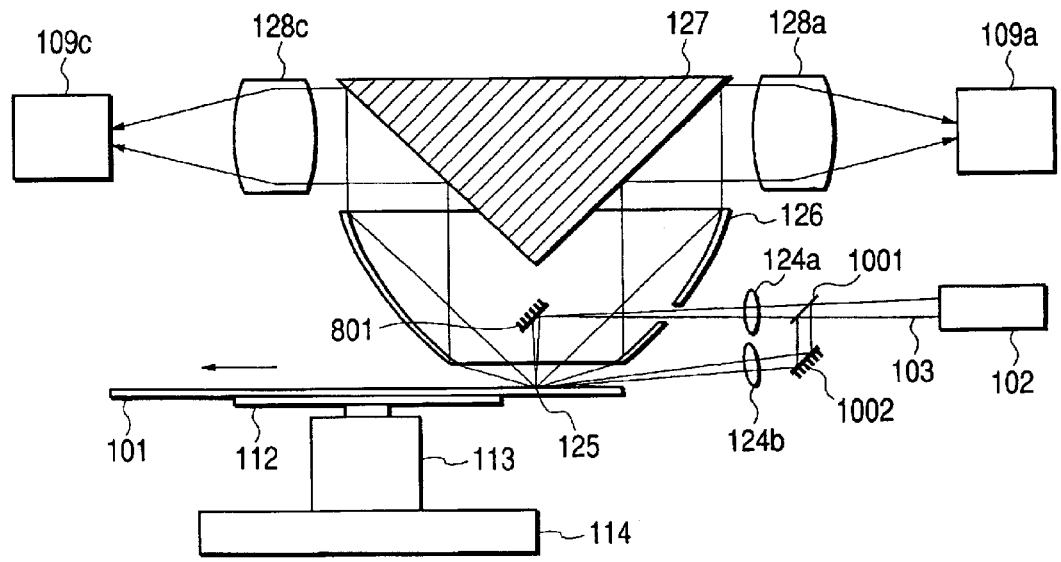
FIG. 22 is a view to show a thirteenth embodiment of the present invention.
Figure 23:
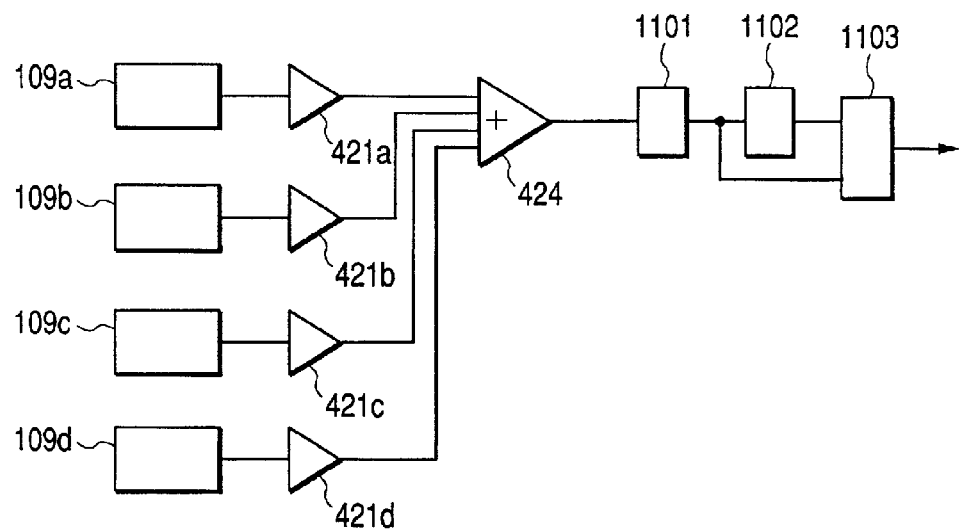
FIG. 23 is a view to show a signal processing circuit of the thirteenth embodiment.

FIGS. 22 and 23 show the thirteenth embodiment of the present invention.

This embodiment is arranged such that the vertical incident illumination of the laser beam where the beam is irradiated from the substantially vertical upper direction with regard to the plane surface of the wafer 101 in the same way as the above eleventh and twelfth embodiments changes over with the slanting illumination of the laser beam where the beam is irradiated slantingly with regard to the wafer in the same way as the above ninth and tenth embodiments. In FIG. 22, the changeover of those illuminations is carried out by the insertion of a mirror 1001 into the light path and the removal thereof from the latter. The arrangement and operation of the curved mirror 126, the pyramidal mirror 127, the condensers 128a to 128d and the photoelectric conversion devices 109a to 109d and so forth are the same as the above ninth embodiment, in which drawing the condensers 128b and 128d as well as the photoelectric conversion devices 109b and 109d are not shown. In case where the mirror 1001 is inserted in the light path of the laser beam, the beam emitted from a laser luminous source 102 is reflected at the mirror 1001, which beam is further reflected at a mirror 1002 and condensed at a condenser 124b so as to be incident to slantingly with regard to the plane surface of the wafer 101 (slanting illumination). On the other hand, in case where the mirror 1001 is removed from the light path of the laser beam, after the beam is condensed at the condenser 124a, the beam directs substantially in parallel with regard to the plane surface of the wafer 101 through the aperture provided on the side surface of the curved mirror 126, which beam is reflected at a mirror 801 provided inside the curved mirror 126 so as to be incident to the substantially vertical direction with regard to the wafer (vertical incident illumination). After the whole surface of the wafer by the vertical incident illumination is detected over, the same illumination is changed over with the slanting illumination by inserting the mirror 1001 in the light path for detecting the whole wafer surface. Then, the detecting results of both vertical and slanting illuminations are compared. The scattered light reflected from the wafer 101 including that to be reflected at the curved mirror 126 is divided into four directions at the pyramidal mirror 127, which scattered light of each direction is condensed at the respective condensers 128a to 128d sop as to be converted into an electrical signal at the respective photoelectric conversion devices 109a to 109d. The signals as obtained are processed at a signal processing circuit as shown in FIG. 23. In FIG. 23, reference numerals 421a to 421d indicate analog processing circuits, and numeral 424 indicates a summing circuit while numerals 1101, 1102 and 1103 indicate a binary circuit, a memory circuit and a comparison circuit, respectively. Amplification and noise processing operation and so forth are carried out at the analog processing circuits 421a to 421d for the respective signals output from the photoelectric conversion devices 109a to 109d, which signals are summed up at the summing circuit 424. At the detecting operation by way of the vertical incident illumination of the laser beam, the value output from the summing circuit 424 is compared with the threshold limit value at the binary circuit 1101, and when the former value results in being greater than a given value, that value and its coordinate are memorized at the memory circuit 1102. At the subsequent detecting operation by way of the slanting illumination, the value output from the summing circuit 424 is compared with the threshold limit value at the binary circuit 1102, and when the former value results in being greater than a given value, that value and its coordinate are compared at the comparison circuit 1103 with the memorized contents of the memory circuit 1102, which result is indicated in the displaying section that is not shown in the drawings. When defect such as scratch or foreign particle in which one coordinate corresponds to the other coordinate is found, the defect and foreign particle are distinguished from each other by the largeness of the detected value while whether the defect or foreign particle is serious or not is determined by the detected signal level.

This embodiment allows a wide range of defect and foreign particle to be detected with high precision, which further facilitates the separate detection between defect such as scratch and foreign particle. The other operation and effect are the same as the above ninth and eleventh embodiments.

Figure 24:
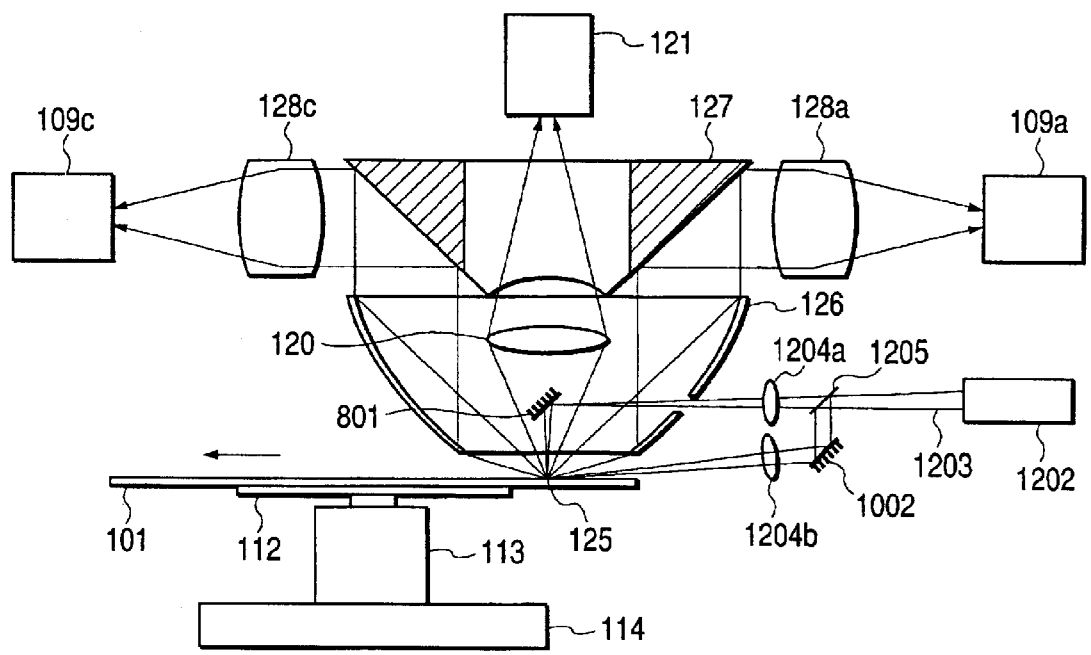
FIG. 24 is a view to show a fourteenth embodiment of the present invention.

FIGS. 24 and 25 show the fourteenth embodiment of the present invention.

This embodiment is arranged such that the vertical incident illumination where the laser beam is irradiated from the substantially vertical upper direction with regard to the plane surface of the wafer 101 in the same way as the above eleventh and twelfth embodiments is changed over with the slanting illumination where the beam is irradiated slantingly with regard to the plane surface thereof in the same way as the above ninth and tenth embodiments, and the detection of the directivity of the scattered light in reflection is carried out by using the scattered light to be reflected in the substantially vertical upper direction with regard to the plane surface of the wafer 101 in the same way as the above twelfth embodiment as well as using the scattered light to be incident to the curved mirror 126 and to be reflected from that mirror. The arrangement and operation of the curved mirror 126, the pyramidal mirror 127, the condensers 128a to 128d and the photoelectric conversion devices 109a to 109d and 121 are the same as the above twelfth embodiment, among which the condensers 128b and 128d as well as the photoelectric conversion devices 109b and 109d are not shown in FIG. 24. In case where a mirror 1205 intervenes in the path of the laser beam, the beam emitted from a laser luminous source 1202 is reflected at the mirror 1205 and further reflected at a mirror 1002, which beam is then condensed at a condenser 1204b so as to be incident slantingly with regard to the plane surface of the wafer 101 (slanting illumination). On the other hand, in case where the mirror 1205 is not in the path of the laser beam, the beam is condensed at the condenser 1204b, which beam directs substantially in parallel with regard to the plane surface of the wafer 101 through the aperture provided on the side surface of the curved mirror 126 and is reflected at a mirror 801 provided inside the curved mirror 126 so as to be incident in the substantially vertical direction towards the wafer 101 (vertical incident illumination). The scattered light to be reflected in the substantially vertical direction with regard to the plane surface of the wafer 101 is condensed at a condenser 120 and is incident to the photoelectric conversion device 121 through the central hole of the pyramidal mirror 127 so as to be converted into an electrical signal. The arrangement and operation of the curved mirror 126, the pyramidal mirror 127, the condensers 128a to 128d and the photoelectric conversion devices 109a to 109d are the same as the above twelfth embodiment. The processing of the signals output from the photoelectric conversion devices 109a to 109d and 121 is carried out by the signal processing circuit as shown in FIG. 25.

Figure 25A:
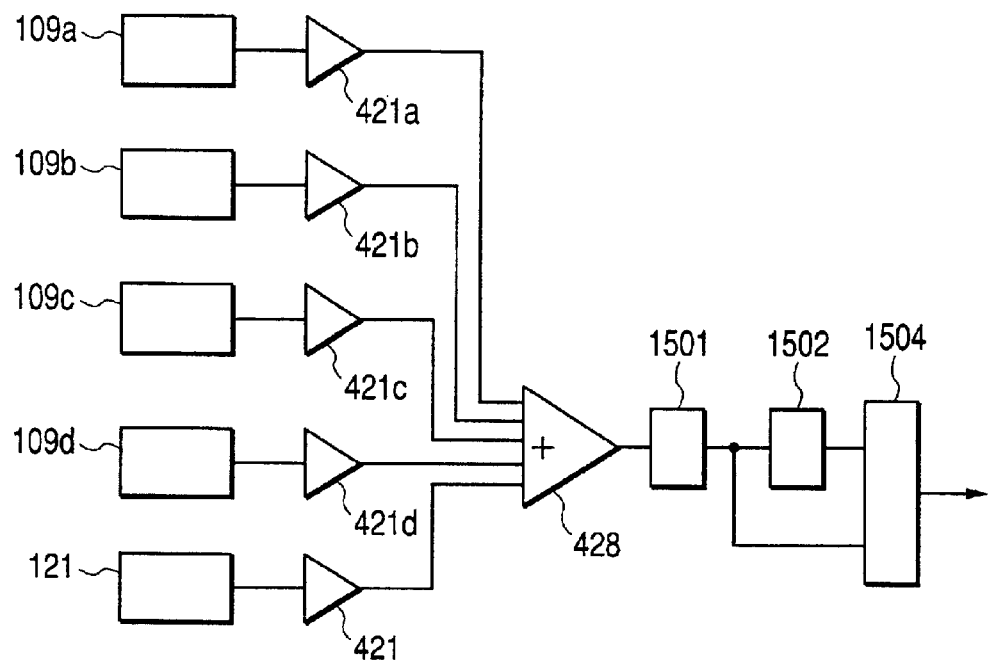
FIG. 25 is a view to show a signal processing circuit of the fourteenth embodiment.
Figure 25B:
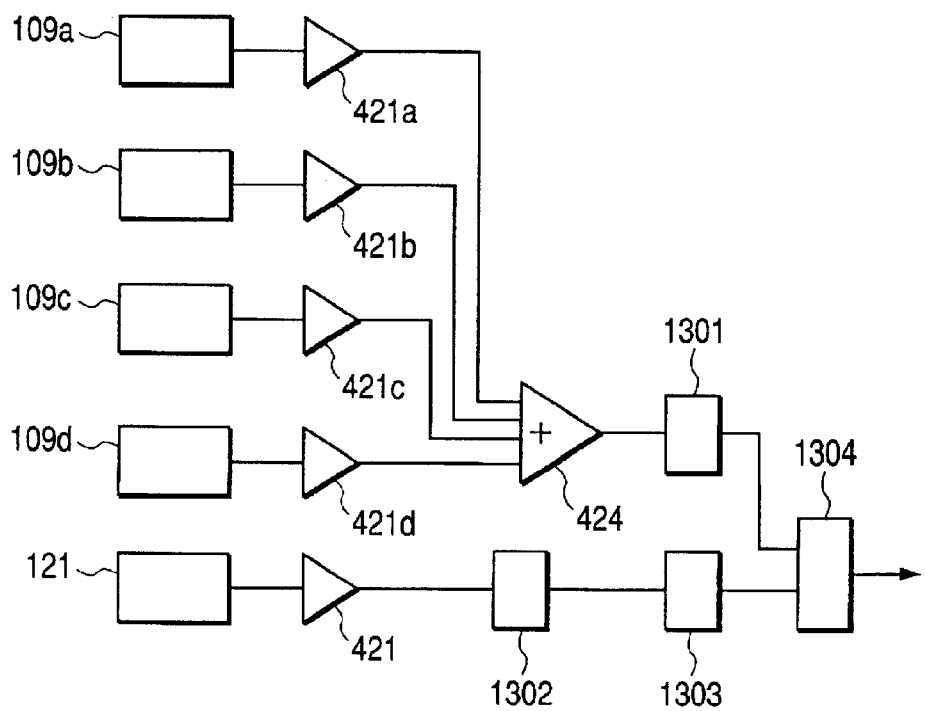

FIG. 25(a) shows the state where the total sum of the signal output from the respective photoelectric conversion devices 109a to 109d and that from the photoelectric conversion device 121 is compared for each case of the vertical incident illumination and the slanting illumination so as to detect the directivity of the scattered light in reflection, while FIG. 25(b) shows the state where the processing result of the signal output from the photoelectric conversion device 121 in the case of the vertical incident illumination is compared with the summing result of the signal output from the respective photoelectric conversion devices 109a to 109d in the case of the slanting illumination so as to detect the directivity of the scattered light in reflection. In either case, the data output from the comparison circuit are input to the displaying section that is not shown in the drawing, on the display of which section the information relevant to the directivity of the scattered light in reflection is indicated such that defect such as scratch and foreign particle are distinguishable.

In FIG. 25(a), at the detecting operation by the vertical incident illumination, amplification and noise processing operation and so forth are carried out at the analog processing circuits 421a to 421d and 421 for the signals output from the photoelectric conversion devices 109a to 109d and 121, which signals are then summed up at the summing circuit 428. The value output from the summing circuit 428 is compared at the binary circuit 1501 with the threshold limit value, and when the former value is greater than a given value, that value and its coordinate are memorized at the memory circuit 1502. At the following slanting illumination, the value output from the summing circuit 428 is compared at the binary circuit 1501 with the threshold limit value, and when the former value is larger than a given value, that value and its coordinate are compared at the comparison circuit 1504 with the memorized contents of the memory circuit 1502, which comparison result is indicated in the displaying section. As a result of it, when defect such as scratch or foreign particle is found in which one coordinate corresponds to the other coordinate, such defect and foreign particle are distinguished from each other by the largeness of the detected value while whether such defect or foreign particle is serious or not is determined by the detected signal level. In FIG. 25(b), at the detecting operation by the vertical incident illumination, amplification and noise processing operation and so forth are carried out at the analog processing circuit 421 for the signal output from the photoelectric conversion device 121, which signal is input to the binary circuit 1302 and is compared with the threshold limit value. When the compared value is larger than a given value, the former value and its coordinate are memorized at the memory circuit 1303. At the detecting operation by the slanting illumination, amplification and noise processing operation and so forth are carried out at the analog processing circuits 421a to 421d for the signals output from the respective photoelectric conversion devices 109a to 109d, which signals are summed up at the summing circuit 424. The value output from the summing circuit 424 is compared with the threshold limit value at the binary circuit 1301, and when the former value is larger than a given value, that value and its coordinate are input to the comparison circuit 1304. At this comparison circuit 1304, the contents input from the binary circuit 1301 are compared with the memorized contents of the memory circuit 1303, which comparison result is indicated on the displaying section, which section is not shown in the drawing. As a result of it, when one coordinate corresponds to the other coordinate, it is determined that there is foreign particle or defect at that coordinate, and defect such as scratch or foreign particle is distinguished by the largeness of the detected value while whether the defect or foreign particle is serious or not is determined by the detected signal level.

In the signal processing circuit as shown in FIG. 25(b), it is arranged such that the signal output from the photoelectric conversion device 121 is adopted for the vertical incident illumination while for the slanting illumination the signals output from the respective photoelectric conversion devices 109a to 109d are adopted, to which the present invention is not limited, but it may be arranged such that both the processed signal output from the photoelectric conversion device 121 and the processed signals output from the respective photoelectric conversion devices 109a to 109d are adopted for each case of the vertical incident illumination and the slanting illumination so as to compare the mutual result in each case.

The above fourteenth embodiment has the effects brought by the above twelfth and thirteenth embodiments. Especially, this embodiment facilitates the detection of defect such as concave scratch as well as to allow such scratch or foreign particle to be detected with high sensitivity and to lighten the weight of the pyramidal mirror 127. The other operation and effect thereof are the same as the above twelfth and thirteenth embodiments.

Figure 26:
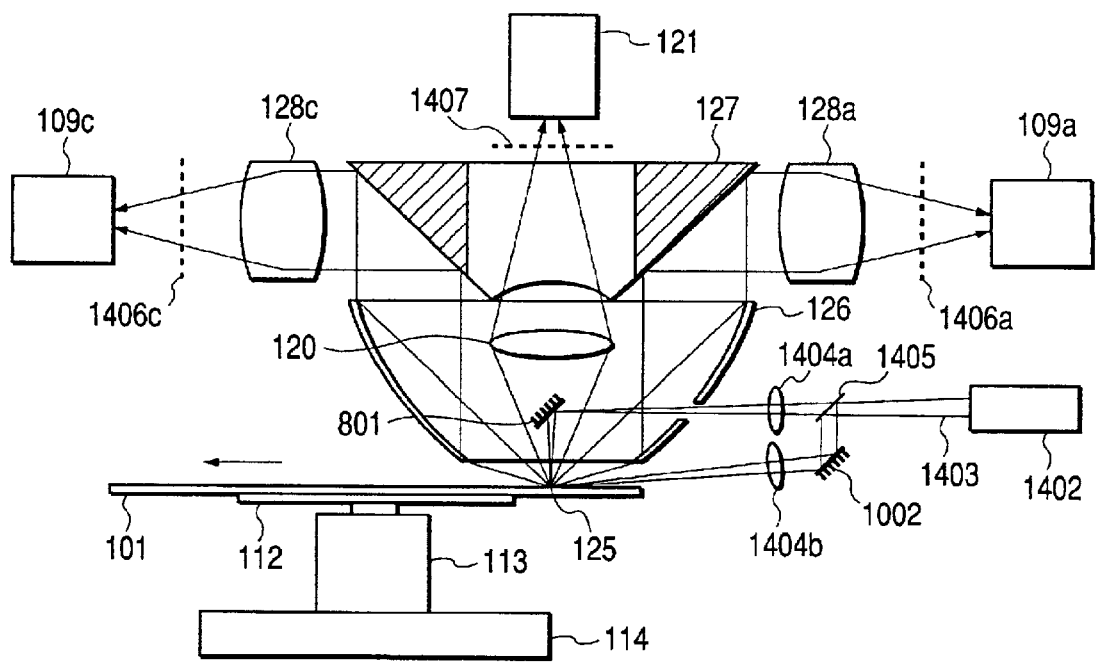
FIG. 26 is a view to show a fifteenth embodiment of the present invention.
Figure 27:
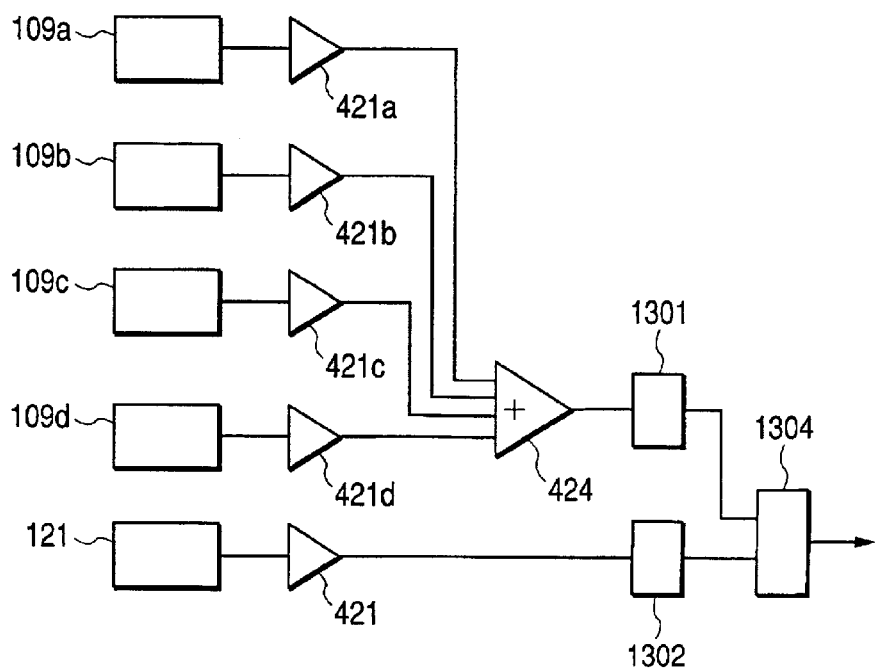
FIG. 27 is a view to show a signal processing circuit of the fifteenth embodiment.

FIGS. 26 and 27 show the fifteenth embodiment of the present invention.

This embodiment is arranged such that the vertical incident illumination and the slanting illumination are carried out simultaneously without the changeover operation. FIG. 26 shows the structural arrangement of the apparatus, and FIG. 27 shows the arrangement of the signal processing circuit. As shown in FIG. 26, the laser beam emitted from a multi-oscillation laser 1402 that is a laser luminous source herein is divided by a wavelength separation mirror 1405 into a beam for the vertical incident illumination and that for the slanting illumination, both of which beams are simultaneously irradiated onto the wafer. The arrangement and operation of the curved mirror 126, the pyramidal mirror 127, the condensers 128a to 128d among which the condensers 128b and 128d are not shown in FIG. 26 and the photoelectric conversion devices 109a to 109d and 111 among which the photoelectric conversion devices 109b and 109d are not shown in FIG. 26, respectively are the same as the above fourteenth embodiment. Sharp cut filters 1406a to 1406d and 1407 are provided in the structural arrangement of this embodiment, and it is arranged such that the photoelectric conversion devices 109a to 109d detect the scattered light by the slanting illumination while the photoelectric conversion device 121 detects the scattered light by the vertical incident illumination. As shown in FIG. 27, amplification and noise processing operation and so forth are carried out at the analog processing circuit 421 for the signal output from the photoelectric conversion device 121 to process the scattered light by the vertical incident illumination, which signal is then input to the binary circuit 1302. At this binary circuit, the detected value is compared with the threshold limit value, and when the former value is it greater than a certain value, that value and its coordinate are input to the comparison circuit 1304. Then, amplification and noise processing operation and so forth are carried out at the analog processing circuits 421a to 421d for the signals output from the respective photoelectric conversion devices 109a to 109d, which signals are then summed up at the summing circuit 424. The value output from the summing circuit 424 is compared with the threshold limit value at the binary circuit 1301, and when the former value is greater than a give value, that value and its coordinate are input to the comparison circuit 1304. At this comparison circuit 1304, the contents input from the binary circuits 1301 and 1302 are compared, which comparison result is indicated at the displaying section that is not shown in the drawings. As a result of it, provided that one coordinate corresponds to the other coordinate, it is determined that there is defect or foreign particle at that coordinate, and defect or foreign particle is distinguished by the largeness of the detected value while whether such defect or foreign particle is serious or not is determined by the detected signal level. The difference between this embodiment and the fourteenth one lies in that the data output from the binary circuit 1302 are not memorized, but directly input to the comparison circuit 1304.

This embodiment allows the detection operation to be performed for a short period of time, because there is no need to carry out the changeover between the vertical incident illumination and the slanting operation, and does not require any structural arrangement for such changeover with the result that it facilitates the arrangement of the incident optical system which is an irradiation means. The other operation and effect thereof are the same as the above fourteenth embodiment.

Figure 28:
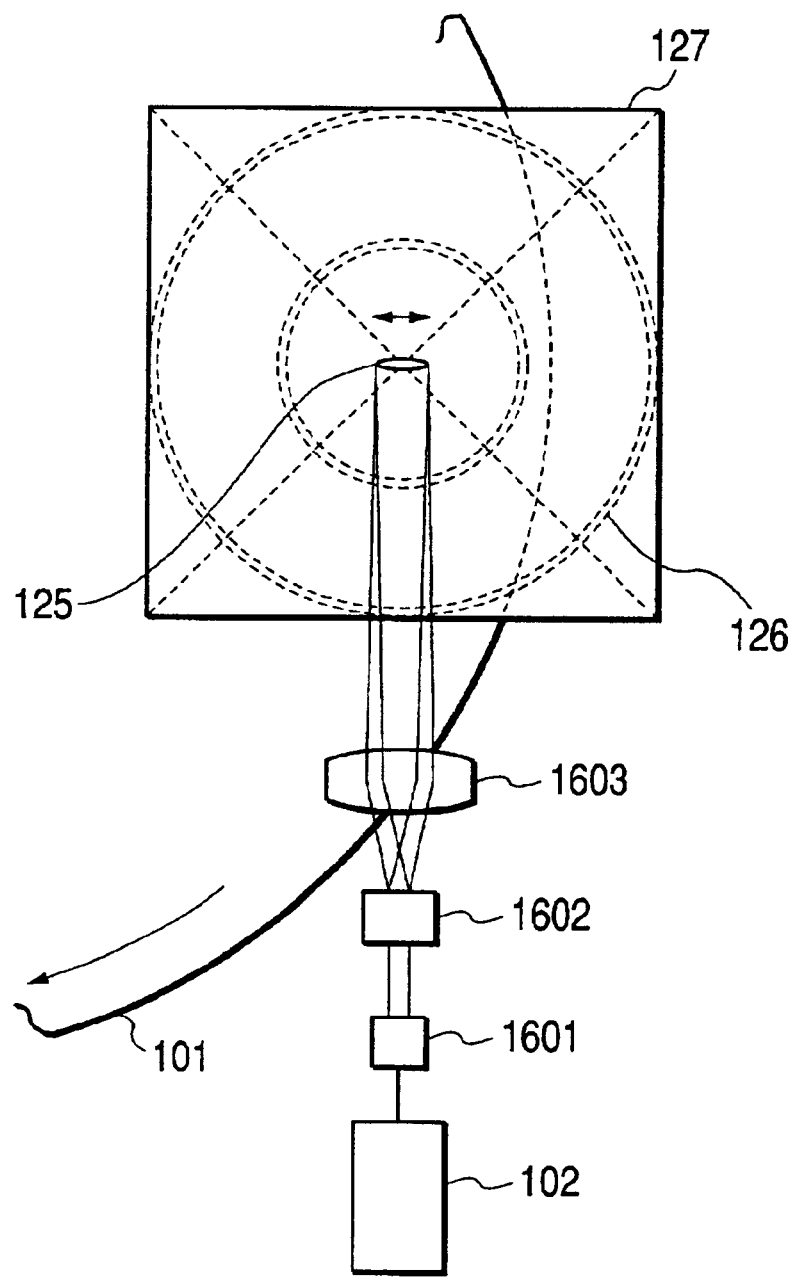
FIG. 28 is a view to show a sixteenth embodiment of the present invention.

FIG. 28 shows the sixteenth embodiment of the present invention.

This embodiment is arranged such that the spiral scanning operation of the wafer that is an object in detection and the laser beam scanning operation are combined wherein the beam emitted from the laser luminous source 102 is expanded at the beam expander 1601, which beam scans with regard to the radius direction of the semiconductor wafer through a scanner. The arrangement of this embodiment is applicable to that of the respective ninth to fifteenth embodiments as mentioned above. A galvanomirror, a polygonmirror or an AOD (Acoustic Optical Deflector) is adoptable for the scanner, for examples.

The present invention is not limited to the scope of the above embodiments, but it may be arranged by combining the features of the respective embodiments as desired. In the above embodiments, the laser beams of two wavelengths are adopted, but those of three or more wavelengths are adoptable. In order to move the laser beam relatively with regard to an object in detection in a spiral manner and as such, it is arranged to impart the revolving operation and the moving operation of the rotational axis to the object in detection, but it may be arranged to impart the relative movement with regard to the object in detection corresponding to the above moving operation of the rotational axis to the laser beam. Moreover, where appropriate, it may be arranged to impart the above relative movement with regard to each other to both the laser beam and the object in detection. The above moving operation of the rotational axis is not limited to the rectilinear movement. As for the division of the incident path of the laser beam with regard to the object in detection, it is arranged such that the incident path is divided into two paths, to which the present invention is not limited, but the number of which path may be three or more. Neither the direction of and the number of the paths to detect the scattered light in reflection nor the position of and the number of the photoelectric conversion devices are limited to the above embodiments. For instance, it may be arranged such that the plurality of paths to detect the scattered light in reflection is provided in the substantially vertical direction with regard to the surface of the object in detection, which paths are detected by as many photoelectric conversion devices. Further, in the above embodiments, a semiconductor wafer is adopted for an example of the object in detection, to which the present invention is not limited, but it can be a thin film substrate, a photomask, a TFT panel, a PDP (Plasma Display Panel) and so forth. Then, as an example of the laser luminous source in the illumination optical system, a UV laser or DUV laser may be adoptable.

It should be appreciated that the present invention is workable in another modified embodiments without deviating from the spirit and the features thereof, and the embodiments as disclosed herein are only some of the examples to be presented in all aspects so that the scope of the present invention should not be limited to the above disclosures. The technical scope of the present invention is recited in the accompanying claims, the modifications and alterations including the equivalents of which recitation belong to the present invention.

What is claimed is:

1. An apparatus for detecting foreign particles and defects, comprising:

an illumination optical system to irradiate a surface of an object substantially simultaneously from different angles using a plurality of laser beams having different wavelengths, irradiation being onto a substantially same location of the object;

a detection section to separately detect each of the laser beams scattered from the object by the irradiation;

a conversion section to convert detected laser beams scattered from the object into an electrical signal; and a processing section to extract a signal corresponding to the foreign particles or defects from the electrical signal converted by the conversion section, and to classify the extracted signal into predetermined foreign particle or defect categories;

wherein an irradiation location of the laser beam moves with regard to a surface of the object.

2. An apparatus according to claim 1, wherein the illumination optical system is arranged such that a laser having the plurality of wavelengths that are simultaneously emitted from a multi-oscillation laser luminous source are separated by each of the wavelengths into the laser beams of the different wavelengths.

3. An apparatus according to claim 1, wherein an irradiation angle of the laser beam with regard to a vertical line taken on the surface of the object includes a range from substantially 60° to 90° as well as a range from substantially 0° to 30°.

4. An apparatus according to claim 1, wherein the plurality of laser beams are cyclically deflected to sub-scan the laser beams with regard to a surface of the object, simultaneously with at least one of rotational and linear movement of the object.

5. An apparatus according to claim 4, wherein the plurality of laser beams are cyclically deflected using at least one of a rotating mirror and an acoustic optical deflector.

6. An apparatus for detecting foreign particles and defects, comprising:

a stage to support and rotate an object being subjected to detection;

an illumination optical system to irradiate a surface of the object substantially simultaneously from different angles using a plurality of laser beams having different wavelengths, irradiation being onto a substantially same location of a surface of the object in a simultaneous scanning operation;

a detection section to separately detect each of the laser beams scattered from the surface by the irradiation;

a conversion section to convert the detected laser beams scattered from the surface into an electrical; and a processing section to extract a signal corresponding to foreign particles or defects from the electrical signal converted by the conversion section, and to classify the extracted signal into predetermined foreign particle or defect categories;

wherein the above plurality of laser beams being irradiated substantially simultaneously moves with regard to the surface of the object in a spiral manner by a relative movement between the stage and illumination optical system.

7. An apparatus according to claim 6, wherein the stage is arranged to move a position of a rotational axis of the object in detection relative to an irradiation position of the laser beam.

8. An apparatus according to claim 6, wherein the plurality of laser beams are cyclically defected to sub-scan the laser beams regard to a surface of the object, simultaneously with at least one of rotational and linear movement of the object.

9. An apparatus according to claim 8, wherein the plurality of laser beams are cyclically deflected using at least one of a rotating mirror and an acoustic optical deflector.

10. A method for detecting foreign particles and defects, comprising:

irradiating a surface of an object substantially simultaneously from different angles using a plurality of laser beams having different wavelengths, irradiation being onto a substantially same location of the object;

detecting by each of the wavelengths, the scattered light reflected from the location of the object;

converting the scattered light of each of the detected wavelengths into an electrical signal; and processing the converted electrical signal to extract a signal corresponding to the foreign particles or defects from the converted electrical signal, and classifying the extracted signal into predetermined foreign particle or defect categories;

wherein an irradiation location of the laser beam moves with regard to a surface of the object.

11. A method according to claim 10, wherein the plurality of laser beams are cyclically deflected to sub-scan the laser beams with regard to a surface of the object, simultaneously with at least one of rotational and linear movement of the object.

12. A method according to claim 11, wherein the plurality of laser beams are cyclically deflected using at least one of a rotating mirror and an acoustic optical deflector.

13. A method for detecting foreign particles and defects, comprising:

supporting and rotating an object;

irradiating a surface of the object substantially simultaneously from different angles using a plurality of laser beams having different wavelengths, irradiation being onto a substantially same location of a surface of the object in a simultaneous scanning operation;

detecting a scattered light reflected from the location of the surface by each of the wavelengths;

converting the scattered light of each of the detected wavelengths into an electrical signal; and processing the converted electrical signal to extract a signal corresponding to foreign particles or defects from the converted electrical signal, and classifying the extracted signal into predetermined foreign particle or defect categories;

wherein the plurality of laser beams moves relative to the surface of the object in a spiral manner.

14. A method according to claim 13, wherein the plurality of laser beams are cyclically deflected to sub-scan the laser beams with regard to a surface of the object, simultaneously with at least one of rotational and linear movement of the object.

15. A method according to claim 14, wherein the plurality of laser beams are cyclically deflected using at least one of a rotating mirror and an acoustic optical deflector.

16. An apparatus for detecting foreign particles and defects, comprising:

an irradiation means for irradiating a first laser beam having a first wavelength onto a portion on a surface of an object in detection from a first incident angle, and a second laser beam having a second wavelength onto the portion of the object from a second incident angle;

a first detection optical system to detect light scattered from the object in detection by the irradiation of the second laser beam;

a second detection optical system to detect light scattered from the object in detection by the irradiation of the second laser beam;

a processing means to process a first signal output from the first detection optical system and a second signal output from the second detection optical system, and to extract a signal corresponding to a foreign particle and a defect respectively; and a means to display a result obtained by the processing means, wherein the object in detection is rotating during the detection.

17. A method according to claim 16, wherein the first and second laser beams are cyclically deflected to sub-scan the laser beams with regard to a surface of the object, simultaneously with at least one of rotational and linear movement of the object.

18. A method according to claim 17, wherein the first and second laser beams are cyclically deflected using at least one of a rotating mirror and an acoustic optical deflector.

* * * * *